(12) United States Patent
Ferguson et al.

(10) Patent No.: US 8,399,637 B2
(45) Date of Patent: Mar. 19, 2013

(54) NUCLEIC ACIDS ENCODING PROTEINS FOR MODULATING NA,K-ATPASE

(75) Inventors: Tanya S. Ferguson, Drexel Hill, PA (US); Irwin Levitan, Philadelphia, PA (US); Susan M. Cibulsky, Washington, DC (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/892,666

(22) Filed: Aug. 24, 2007

(65) Prior Publication Data

US 2008/0181901 A1    Jul. 31, 2008

Related U.S. Application Data

(60) Provisional application No. 60/853,326, filed on Aug. 24, 2006.

(51) Int. Cl.
*C07H 21/04* (2006.01)
*C12N 15/64* (2006.01)
*C12Q 1/68* (2006.01)

(52) U.S. Cl. ....... 536/23.1; 435/6.1; 435/91.4; 536/24.2

(58) Field of Classification Search ........................ None
See application file for complete search history.

(56) References Cited

U.S. PATENT DOCUMENTS

2002/0061582 A1 *  5/2002  Albers et al. ............... 435/254.2

FOREIGN PATENT DOCUMENTS

WO    WO 00/73469    * 12/2000

OTHER PUBLICATIONS

Levitan, I.B., 2005, Journal of Neurochemistry, August , vol. 94, Supplement No. 2 p. 158.*
Bidard J. N. et al., Biochem. Biophys. Acta., 769:245, 1984.
Cantley L. C. Jr. et al., J. Biol. Chem., 243:7361-7368, 1978.
Horwitz B. A., Fed. Proc., 38:2170-2176, 1979.
Mao et al., "MONaKA, a Novel Modulator of the Plasma Membrane Na, K-ATPase", The Journal of Neuroscience, Aug. 31, 2005; 25(35):7934-7943.
Phillis J. W., Cell, Tissue and Organ Cultures in Neurobiology, pp. 93-97, 1978.
Rossier B. C. et al., Sceince, 12:483-487, 1987.
Smith T. J. et al., Fed. Proc., 38:2150-2153, 1979.
Tamura M. et al., J. Biol. Chem., 260:9672, 1985.

* cited by examiner

*Primary Examiner* — Robert Landsman
*Assistant Examiner* — Ian Dang
(74) *Attorney, Agent, or Firm* — Mark S. Cohen; Pearl Cohen Zedek Latzer, LLP

(57) ABSTRACT

This invention relates to an isolated protein MONaKA and methods of its use. Specifically, the invention is directed to a protein that modulates the Na,K-ATPase and glutamate transporters, by binding to the b-subunit of the plasma membrane Na,K-ATPase (Na pump).

6 Claims, 8 Drawing Sheets

A

B

SEQUENCE LISTING

<160> NUMBER OF SEQ ID NOS: 20

<210> SEQ ID NO 1
<211> LENGTH: 581
<212> TYPE: PRT
<213> ORGANISM: Murine

<400> SEQUENCE: 1

```
Met Ala Phe Met Glu Lys Pro Pro Ala Gly Lys Val Leu Leu Asp Asp
1               5                   10                  15

Thr Val Pro Leu Thr Ala Ala Val Glu Ala Ser Gln Ser Leu Gln Ser
            20                  25                  30

His Thr Glu Tyr Ile Ile Arg Val Gln Arg Gly Ile Ser Ala Glu Asn
        35                  40                  45

Ser Trp Gln Ile Val Arg Arg Tyr Ser Asp Phe Asp Leu Leu Asn Asn
    50                  55                  60

Ser Leu Gln Ile Thr Gly Leu Ser Leu Pro Leu Pro Pro Lys Lys Leu
65                  70                  75                  80

Ile Gly Asn Met Asp Arg Glu Phe Ile Ala Glu Arg Gln Arg Gly Leu
                85                  90                  95

Gln Asn Tyr Leu Asn Val Ile Met Ala Asn His Val Leu Ser Asn Cys
            100                 105                 110
```

-continued

```
Glu Leu Leu Lys Lys Phe Leu Asp Pro Asn Asn Tyr Ser Ala Asn Tyr
        115                 120                 125

Thr Glu Ile Ala Leu Gln Gln Val Ser Met Phe Phe Arg Ser Glu Pro
    130                 135                 140

Lys Trp Glu Val Val Glu Pro Leu Lys Asp Ile Gly Trp Arg Ile Arg
145                 150                 155                 160

Lys Lys Tyr Phe Leu Met Lys Ile Lys Asn Gln Pro Lys Glu Arg Leu
                165                 170                 175

Val Leu Ser Trp Ala Asp Leu Gly Pro Asp Lys Tyr Leu Ser Asp Lys
            180                 185                 190

Asp Phe Gln Cys Leu Ile Lys Leu Leu Pro Ser Cys Val His Pro Tyr
        195                 200                 205

Ile Tyr Arg Val Thr Phe Ala Thr Ala Ser Glu Ser Ser Ala Leu Leu
    210                 215                 220

Ile Arg Ala Phe Asn Glu Lys Gly Thr Leu Lys Asp Leu Ile Tyr Lys
225                 230                 235                 240

Ala Lys Pro Lys Asp Pro Phe Leu Lys Lys Tyr Cys Asn Pro Lys Lys
                245                 250                 255

Thr Gln Gly Leu Glu Leu Gln Gln Ile Lys Thr Tyr Gly Arg Gln Ile
            260                 265                 270

Leu Glu Ala Leu Lys Phe Leu His Asp Lys Gly Phe Pro Tyr Gly His
        275                 280                 285

Leu His Ala Ala Asn Val Met Leu Asp Gly Asn Thr Cys Arg Leu Leu
    290                 295                 300

Asp Leu Glu Asn Ser Leu Leu Gly Leu Pro Ser Phe Tyr Arg Ser Tyr
305                 310                 315                 320

Phe Thr Gln Phe Arg Lys Ile Asn Thr Leu Glu Ser Val Asp Val His
                325                 330                 335

Cys Phe Gly His Leu Leu Tyr Glu Met Thr Tyr Gly Arg Pro Pro Asp
            340                 345                 350

Ser Val Pro Val Asp Ser Phe Pro Ala Ser Ser Leu Ala Val Val
        355                 360                 365

Ala Val Leu Glu Ser Thr Leu Ser Cys Glu Ala Cys Lys Asn Gly Met
    370                 375                 380

Pro Thr Val Ser Arg Leu Leu Gln Met Pro Leu Phe Ser Asp Val Leu
385                 390                 395                 400

Leu Thr Thr Ser Glu Lys Pro Gln Phe Lys Ile Pro Thr Lys Leu Lys
                405                 410                 415

Glu Ala Leu Arg Ile Ala Lys Glu Cys Ile Glu Lys Arg Leu Thr Glu
            420                 425                 430

Glu Gln Lys Gln Ile His Gln His Arg Arg Leu Thr Arg Ala Gln Ser
        435                 440                 445

His His Gly Ser Glu Glu Glu Arg Lys Arg Arg Lys Ile Leu Ala Arg
    450                 455                 460

Lys Lys Ser Lys Arg Ser Ala Val Glu Asn Ser Glu Glu Gln Pro Val
465                 470                 475                 480

Lys His Ser Asn Ser Asn Asn Ser Gly Ser Gly Ala Ser Ser Pro Leu
                485                 490                 495

Thr Ser Pro Ser Ser Pro Thr Pro Ser Thr Ala Gly Leu Ser Ser
            500                 505                 510

Ala Leu Pro Pro Pro Pro Pro Pro Pro Pro Pro Pro Pro Ala
        515                 520                 525

Gly Pro Ser Pro Thr Ser Ala Thr Glu Met Pro Ala Pro Phe Leu Pro
530                 535                 540
```

```
Gln Pro Val Asn Gly Val Asn Arg Gly Ala Leu Leu Ser Ser Ile Gln
545                 550                 555                 560

Asn Phe Gln Lys Gly Thr Leu Arg Lys Ala Gln Thr Cys Asp His Ser
                565                 570                 575

Ala Pro Lys Ile Gly
            580

<210> SEQ ID NO 2
<211> LENGTH: 1746
<212> TYPE: DNA
<213> ORGANISM: Murine

<400> SEQUENCE: 2
atggccttca tggagaagcc gccggctggc aaggtgctgc tggacgacac ggtgccgctg      60
acagcggccg tcgaggcgag ccagagtctg cagtcgcaca cggaatatat catccgggtg     120
caaagaggaa tttctgcaga aacagctgg cagatcgtca agatacag tgacttcgat        180 ctgcttaaca acagcttgca aattacaggc ctgagcctgc tcttcctcc taagaaactg      240 attggaaaca tggaccgtga gttcatcgct gagaggcagc gaggcctgca gaactacctt     300
aacgtcatca tggcaaatca tgtcttgtcc aactgtgagc tgcttaagaa gttcctagac     360
ccaaacaact attctgcaaa ctatactgag atcgccttac agcaggtttc catgttcttc     420
cgatcagaac aaagtgggga ggtggtagaa ccactgaagg acataggttg gaggataagg     480
aagaaatatt tcttgatgaa aataaaaaac caaccaaagg agcggctggt gctaagctgg     540
gctgatcttg gcccagacaa gtacttgtca gataaagatt ttcagtgtct aatcaaactt     600
ctgccttcct gtgtgcaccc ttacatctat cgggtcacct ttgccacggc tagcgagtcc     660
tccgcattgc tgattagagc ctttaatgag aagggaactt tgaaggatct gatctacaag     720
gcaaaaccaa aggaccccctt cctaaagaaa tactgcaacc taagaaaaac ccagggcctt     780
gaactccagc aaataaaaac atatgggcgg cagatattag aggcactaaa gtttcttcat     840
gacaagggat cccttacgg ccacctccat gcagccaatg tgatgctgga tgcaacact      900 tgccggctgc tagacctcga aaactcactg ctgggtctgc cttccttcta ccgatcctac     960
ttcacacaat tcaggaaaat caatacattg gagagtgtag atgtgcactg ttttggccac    1020
ttactctatg aaatgactta tggacgacct cccgactccg tgcctgtgga ctcctttcct    1080
cctgcatcat ccttggctgt ggtggccgta ttggagtcta cgctgtcttg tgaagcctgt    1140
aaaaatggca tgcctaccgt ctcccggctc ttacagatgc cattattcag tgatgtttta    1200
ctaacaactt ctgaaaagcc acagtttaag attcccacaa aactaaaaga ggcattgcga    1260
attgccaagg aatgcataga aagagactc accgaggaac agaagcagat tcaccagcat    1320
cgaagactaa cgagagccca gtcacaccat gggtctgagg aagaaaggaa aaggagaaag    1380
atcttagctc gaaagaagtc aaaacgatct gctgttgaaa acagtgagga gcagccagtg    1440
aagcacagta actccaataa ctcaggatct ggggccagct caccctctcac atccccatca    1500 tctccaactc caccctccac agcaggactg tcttcagcat tacctccacc tcctccgcca    1560
cctcctcctc cacctccacc agcaggtccc tcgccaacct cagccacgga gatgcctgct    1620
ccgttcctgc cccagcctgt gaatggtgtg aaccgtgggg ccttgctcag ttccatccag    1680
aatttccaaa aggggacttt gcggaaagcc caaacctgtg atcacagcgc tcccaagatc    1740
ggctga                                                               1746
```

<210> SEQ ID NO 3
<211> LENGTH: 515
<212> TYPE: PRT
<213> ORGANISM: Murine
<400> SEQUENCE: 3

```
Met Ala Phe Met Glu Lys Pro Pro Ala Gly Lys Val Leu Leu Asp Asp
1               5                   10                  15

Thr Val Pro Leu Thr Ala Val Glu Ala Ser Gln Ser Leu Gln Ser
            20                  25                  30

His Thr Glu Tyr Ile Ile Arg Val Gln Arg Gly Ile Ser Ala Glu Asn
                35                  40                  45

Ser Trp Gln Ile Val Arg Arg Tyr Ser Asp Phe Asp Leu Leu Asn Asn
    50                  55                  60

Ser Leu Gln Ile Thr Gly Leu Ser Leu Pro Leu Pro Pro Lys Lys Leu
65                  70                  75                  80

Ile Gly Asn Met Asp Arg Glu Phe Ile Ala Glu Arg Gln Arg Gly Leu
                85                  90                  95

Gln Asn Tyr Leu Asn Val Ile Met Ala Asn His Val Leu Ser Asn Cys
                100                 105                 110

Glu Leu Leu Lys Lys Phe Leu Asp Pro Asn Asn Tyr Ser Ala Asn Tyr
            115                 120                 125

Thr Glu Ile Ala Leu Gln Gln Val Ser Met Phe Phe Arg Ser Glu Pro
            130                 135                 140

Lys Trp Glu Val Val Glu Pro Leu Lys Asp Ile Gly Trp Arg Ile Arg
145                 150                 155                 160

Lys Lys Tyr Phe Leu Met Lys Ile Lys Asn Gln Pro Lys Glu Arg Leu
                165                 170                 175

Val Leu Ser Trp Ala Asp Leu Gly Pro Asp Lys Tyr Leu Ser Asp Lys
            180                 185                 190

Asp Phe Gln Cys Leu Ile Lys Leu Leu Pro Ser Cys Val His Pro Tyr
            195                 200                 205

Ile Tyr Arg Val Thr Phe Ala Thr Ala Ser Glu Ser Ser Ala Leu Leu
        210                 215                 220

Ile Arg Ala Phe Asn Glu Lys Gly Thr Leu Lys Asp Leu Ile Tyr Lys
225                 230                 235                 240

Ala Lys Pro Lys Asp Pro Phe Leu Lys Lys Tyr Cys Asn Pro Lys Lys
                245                 250                 255

Thr Gln Gly Leu Glu Leu Gln Gln Ile Lys Thr Tyr Gly Arg Gln Ile
            260                 265                 270

Leu Glu Ala Leu Lys Phe Leu His Asp Lys Gly Phe Pro Tyr Gly His
        275                 280                 285

Leu His Ala Ala Asn Val Met Leu Asp Gly Asn Thr Cys Arg Leu Leu
    290                 295                 300

Asp Leu Glu Asn Ser Leu Leu Gly Leu Pro Ser Phe Tyr Arg Ser Tyr
305                 310                 315                 320

Phe Thr Gln Phe Arg Lys Ile Asn Thr Leu Glu Ser Val Asp Val His
                325                 330                 335

Cys Phe Gly His Leu Leu Tyr Glu Met Thr Tyr Gly Arg Pro Pro Asp
            340                 345                 350

Ser Val Pro Val Asp Ser Phe Pro Pro Ala Ser Ser Leu Ala Val Val
        355                 360                 365

Ala Val Leu Glu Ser Thr Leu Ser Cys Glu Ala Cys Lys Asn Gly Met
370                 375                 380
```

```
Pro Thr Val Ser Arg Leu Leu Gln Met Pro Leu Phe Ser Asp Val Leu
385                 390                 395                 400

Leu Thr Thr Ser Glu Lys Pro Gln Phe Lys Ile Pro Thr Lys Leu Lys
            405                 410                 415

Glu Ala Leu Arg Ile Ala Lys Glu Cys Ile Glu Lys Arg Leu Thr Glu
        420                 425                 430

Glu Gln Lys Gln Ile His Gln His Arg Arg Leu Thr Arg Ala Gln Ser
    435                 440                 445

His His Gly Ser Glu Glu Arg Lys Arg Arg Lys Ile Leu Ala Arg
450                 455                 460

Lys Lys Ser Lys Arg Ser Ala Val Glu Asn Ser Glu Glu Gln Pro Val
465                 470                 475                 480

Lys His Ser Asn Ser Asn Asn Ser Ala Gly Ser Gly Ala Ser Ser Pro
            485                 490                 495

Leu Thr Ser Pro Ser Ser Pro Thr Pro Pro Ser Thr Ala Val Glu His
            500                 505                 510

Ala Pro Leu
    515

<210> SEQ ID NO 4
<211> LENGTH: 1782
<212> TYPE: DNA
<213> ORGANISM: Murine

<400> SEQUENCE: 4
atggccttca tggagaagcc gccggctggc aaggtgctgc tggacgacac ggtgccgctg      60
acagcggccg tcgaggcgag ccagagtctg cagtcgcaca cggaatatat catccgggtg     120
caaagaggaa tttctgcaga aaacagctgg cagatcgtca agatacagtg acttcgat      180 ctgcttaaca acagcttgca aattacaggc ctgagcctgc tcttcctcc taagaaactg      240 attggaaaca tggaccgtga gttcatcgct gagaggcagc gaggcctgca gaactacctt     300
aacgtcatca tggcaaatca tgtcttgtcc aactgtgagc tgcttaagaa gttcctagac     360
ccaaacaact attctgcaaa ctatactgag atcgccttac agcaggtttc catgttcttc     420
cgatcagaac caaagtggga ggtggtagaa ccactgaagg acataggttg gaggataagg     480
aagaaatatt tcttgatgaa aataaaaaac caaccaaagg agcggctggt gctaagctgg     540
gctgatcttg gcccagacaa gtacttgtca gataaagatt ttcagtgtct aatcaaactt     600
ctgccttcct gtgtgcaccc ttacatctat cgggtcacct ttgccacggc tagcgagtcc     660
tccgcattgc tgattagagc ctttaatgag aagggaactt tgaaggatct gatctacaag     720
gcaaaaccaa aggacccctt cctaaagaaa tactgcaacc taagaaaaac ccagggcctt     780
gaactccagc aaataaaaac atatgggcgg cagatattag aggcactaaa gtttcttcat     840
gacaagggat tcccttacgg ccacctccat gcagccaatg tgatgctgga tgcaacact      900 tgccggctgc tagacctcga aaactcactg ctgggtctgc cttccttcta ccgatcctac     960
ttcacacaat tcaggaaaat caatacattg gagagtgtag atgtgcactg ttttggccac    1020
ttactctatg aaatgactta tggacgacct cccgactccg tgcctgtgga ctccttcct     1080 cctgcatcat ccttggctgt ggtggccgta ttggagtcta cgctgtcttg tgaagcctgt    1140
aaaaatggca tgcctaccgt ctcccggctc ttacagatgc cattattcag tgatgttta    1200 ctaacaactt ctgaaaagcc acagtttaag attcccacaa actaaaaga ggcattgcga    1260 attgccaagg aatgcataga aaagagactc accgaggaac agaagcagat tcaccagcat    1320
cgaagactaa cgagagccca gtcacaccat gggtctgagg aagaaaggaa aaggagaaag    1380
```

-continued

```
atcttagctc gaaagaagtc aaaacgatct gctgttgaaa acagtgagga gcagccagtg    1440
aagcacagta actccaataa ctcagcagga tctggggcca gctcacctct cacatcccca    1500
tcatctccaa ctccaccctc cacagcagta gagcatgcac cactttgaac gtgaattttc    1560
ggactgtctt cagcattacc tccacctcct ccgccacctc ctcctccacc tccaccagca    1620
ggtccctcgc caacctcagc cacggagatg cctgctccgt tcctgcccca gcctgtgaat    1680
ggtgtgaacc gtggggcctt gctcagttcc atccagaatt tccaaaaggg aactttgcgg    1740
aaagcccaaa cctgtgatca cagcgctccc aagatcggct ga                      1782
```

<210> SEQ ID NO 5
<211> LENGTH: 467
<212> TYPE: PRT
<213> ORGANISM: Human

<400> SEQUENCE: 5

```
Ser Trp Gln Ile Val Arg Arg Tyr Ser Asp Phe Asp Leu Leu Asn Asn
 1               5                  10                  15

Ser Leu Gln Ile Ala Gly Leu Ser Leu Pro Leu Pro Pro Lys Lys Leu
                20                  25                  30

Ile Gly Asn Met Asp Arg Glu Phe Ile Ala Glu Arg Gln Lys Gly Leu
            35                  40                  45

Gln Asn Tyr Leu Asn Val Ile Thr Thr Asn His Ile Leu Ser Asn Cys
        50                  55                  60

Glu Leu Val Lys Lys Phe Leu Asp Pro Asn Asn Tyr Ser Ala Asn Tyr
    65                  70                  75                  80

Thr Glu Ile Ala Leu Gln Gln Val Ser Met Phe Arg Ser Glu Pro
                85                  90                  95

Lys Trp Glu Val Val Glu Pro Leu Lys Asp Ile Gly Trp Arg Ile Arg
            100                 105                 110

Lys Lys Tyr Phe Leu Met Lys Ile Lys Asn Gln Pro Lys Glu Arg Leu
        115                 120                 125

Val Leu Ser Trp Ala Asp Leu Gly Pro Asp Lys Tyr Leu Ser Asp Lys
    130                 135                 140

Asp Phe Gln Cys Leu Ile Lys Leu Leu Pro Ser Cys Leu His Pro Tyr
145                 150                 155                 160

Ile Tyr Arg Val Thr Phe Ala Thr Ala Asn Glu Ser Ser Ala Leu Leu
                165                 170                 175

Ile Arg Met Phe Asn Glu Lys Gly Thr Leu Lys Asp Leu Ile Tyr Lys
            180                 185                 190

Ala Lys Pro Lys Asp Pro Phe Leu Lys Lys Tyr Cys Asn Pro Lys Lys
        195                 200                 205

Ile Gln Gly Leu Glu Leu Gln Gln Ile Lys Thr Tyr Gly Arg Gln Ile
    210                 215                 220

Leu Glu Val Leu Lys Phe Leu His Asp Lys Gly Phe Pro Tyr Gly His
225                 230                 235                 240

Leu His Ala Ser Asn Val Met Leu Asp Gly Asp Thr Cys Arg Leu Leu
                245                 250                 255

Asp Leu Glu Asn Ser Leu Leu Gly Leu Pro Ser Phe Tyr Arg Ser Tyr
            260                 265                 270

Phe Ser Gln Phe Arg Lys Ile Asn Thr Leu Glu Ser Val Asp Val His
        275                 280                 285

Cys Phe Gly His Leu Leu Tyr Glu Met Thr Tyr Gly Arg Pro Pro Asp
    290                 295                 300
```

```
Ser Val Pro Val Asp Ser Phe Pro Ala Pro Ser Met Ala Val Val
305                 310                 315                 320

Ala Val Leu Glu Ser Thr Leu Ser Cys Glu Ala Cys Lys Asn Gly Met
                325                 330                 335

Pro Thr Ile Ser Arg Leu Leu Gln Met Pro Leu Phe Ser Asp Val Leu
            340                 345                 350

Leu Thr Thr Ser Glu Lys Pro Gln Phe Lys Ile Pro Thr Lys Leu Lys
        355                 360                 365

Glu Ala Leu Arg Ile Ala Lys Glu Cys Ile Glu Lys Arg Leu Ile Glu
370                 375                 380

Glu Gln Lys Gln Ile His Gln His Arg Arg Leu Thr Arg Ala Gln Ser
385                 390                 395                 400

His His Gly Ser Glu Glu Glu Arg Lys Lys Arg Lys Ile Leu Ala Arg
                405                 410                 415

Lys Lys Ser Lys Arg Ser Ala Leu Glu Asn Ser Glu Glu His Ser Ala
            420                 425                 430

Lys Tyr Ser Asn Ser Asn Asn Ser Ala Gly Ser Gly Ala Ser Ser Pro
        435                 440                 445

Leu Thr Ser Pro Ser Ser Pro Thr Pro Pro Ser Thr Ser Val Glu His
    450                 455                 460

Ala Pro Phe
465

<210> SEQ ID NO 6
<211> LENGTH: 1770
<212> TYPE: DNA
<213> ORGANISM: Human

<400> SEQUENCE: 6
atggccttca tggagaagcc gccagccggc aaggtgctgc tggacgacac ggtgccgctg      60
acagcagcca tcgaggcgag ccagagcctg cagtcccaca cggaatatat tattcgagtg     120
caaagaggaa tttctgtgga aaacagctgg cagattgtta aagatacag tgactttgat      180 ttgcttaaca acagcttaca gattgcaggc ctaagtctac ctcttcctcc caaaaaattg     240
attggtaaca tggatcgtga attcatagct gaaaggcaga aaggtcttca gaactatctc     300
aacgtgatca caacaaatca tatcttgtct aattgtgagc tggttaagaa gttttttagat    360 ccaaacaact attccgcaaa ctatactgag attgccttgc aacaggtttc catgttcttc     420
cgatcagaac aaagtgggag ggtggtggaa cctttgaaag acataggttg agagaataagg     480 aagaaatatt tcttgatgaa gattaaaaat cagccaaagg aacggctagt gttaagctgg     540
gctgaccttg cccagacaa gtatttgtca gataaagatt ttcagtgtct aatcaaactt      600
ctgccttctt gtttgcaccc ttacatctat cgggttacct ttgccacagc taatgaatcc     660
tcagcgttgc ttattaggat gtttaacgaa aagggaacat tgaaggatct gatctacaag     720
gcaaaaccaa agacccatt tctaaagaag tactgcaacc taagaagat tcagggcctg       780 gaactccagc aaataaaaac atatggacgg caaatattag aggtactgaa gtttcttcat     840
gacaagggat ccccttatgg gcatcttcac gcctccaatg tgatgctcga tggggacact     900
tgtcggctgc tggaccttga gaattcctta ttgggcctgc ttccttcta ccgatcttat      960 ttttcacaat tcaggaaaat caatacattg gaaagtgtgg atgtccactg ctttggccac    1020
ttactgtatg aaatgactta tggacgaccg ccagactcgg tgcctgtgga ctccttccct    1080
cctgccccgt ccatggctgt ggtggccgtg ttggagtcta cgctgtcttg tgaagcctgt    1140
aaaaatggca tgcctaccat ctcccggctc ttacagatgc cattattcag cgatgttta    1200
```

-continued

```
ctaaccactt ctgaaaaacc acagtttaag atccctacaa agttaaaaga ggcattgaga    1260
attgccaaag aatgtataga gaagagacta attgaggaac agaaacagat tcaccagcat    1320
cgaagactga caagagctca gtcccaccat ggatctgagg aggaaagaaa aaaagaaag     1380 attttagctc gaaagaagtc aaaacgatct gctcttgaaa atagtgaaga gcattcagcg    1440
aagtacagca actccaataa ttcagcagga tctggggcca gctcacctct cacgtccccg    1500
tcatcgccaa ctcccccctc tacatcagta gagcatgcac cattttgaac gtgaattttc    1560
gggatatctg cattacctcc acctcctcca cctccaccac caccagcagc tcccttgcct    1620
cctgcgagca ccgaggcacc tgcccagctc tcgtctcagg ctgtgaatgg catgagccga    1680
ggggccttgc tcagctccat ccagaatttc caaaaaggaa ctttgaggaa agccaaaacc    1740
tgtgatcaca gtgctccgaa gatcggctga                                     1770
```

<210> SEQ ID NO 7
<211> LENGTH: 578
<212> TYPE: PRT
<213> ORGANISM: Human

<400> SEQUENCE: 7

```
Met Ala Phe Met Glu Lys Pro Pro Ala Gly Lys Val Leu Leu Asp Asp
1               5                   10                  15

Thr Val Pro Leu Thr Ala Ala Ile Glu Ala Ser Gln Ser Leu Gln Ser
            20                  25                  30

His Thr Glu Tyr Ile Ile Arg Val Gln Arg Gly Ile Ser Val Glu Asn
        35                  40                  45

Ser Trp Gln Ile Val Arg Arg Tyr Ser Asp Phe Asp Leu Leu Asn Asn
    50                  55                  60

Ser Leu Gln Ile Ala Gly Leu Ser Leu Pro Pro Pro Lys Lys Leu
65                  70                  75                  80

Ile Gly Asn Met Asp Arg Glu Phe Ile Ala Glu Arg Gln Lys Gly Leu
                85                  90                  95

Gln Asn Tyr Leu Asn Val Ile Thr Thr Asn His Ile Leu Ser Asn Cys
            100                 105                 110

Glu Leu Val Lys Lys Phe Leu Asp Pro Asn Asn Tyr Ser Ala Asn Tyr
        115                 120                 125

Thr Glu Ile Ala Leu Gln Gln Val Ser Met Phe Phe Arg Ser Glu Pro
    130                 135                 140

Lys Trp Glu Val Val Glu Pro Leu Lys Asp Ile Gly Trp Arg Ile Arg
145                 150                 155                 160

Lys Lys Tyr Phe Leu Met Lys Ile Lys Asn Gln Pro Lys Glu Arg Leu
                165                 170                 175

Val Leu Ser Trp Ala Asp Leu Gly Pro Asp Lys Tyr Leu Ser Asp Lys
            180                 185                 190

Asp Phe Gln Cys Leu Ile Lys Leu Leu Pro Ser Cys Leu His Pro Tyr
        195                 200                 205

Ile Tyr Arg Val Thr Phe Ala Thr Ala Asn Glu Ser Ser Ala Leu Leu
    210                 215                 220

Ile Arg Met Phe Asn Glu Lys Gly Thr Leu Lys Asp Leu Ile Tyr Lys
225                 230                 235                 240

Ala Lys Pro Lys Asp Pro Phe Leu Lys Lys Tyr Cys Asn Pro Lys Lys
                245                 250                 255

Ile Gln Gly Leu Glu Leu Gln Gln Ile Lys Thr Tyr Gly Arg Gln Ile
            260                 265                 270
```

```
Leu Glu Val Leu Lys Phe Leu His Asp Lys Gly Phe Pro Tyr Gly His
        275                 280                 285
Leu His Ala Ser Asn Val Met Leu Asp Gly Asp Thr Cys Arg Leu Leu
    290                 295                 300
Asp Leu Glu Asn Ser Leu Leu Gly Leu Pro Ser Phe Tyr Arg Ser Tyr
305                 310                 315                 320
Phe Ser Gln Phe Arg Lys Ile Asn Thr Leu Glu Ser Val Asp Val His
                325                 330                 335
Cys Phe Gly His Leu Leu Tyr Glu Met Thr Tyr Gly Arg Pro Pro Asp
            340                 345                 350
Ser Val Pro Val Asp Ser Phe Pro Pro Ala Pro Ser Met Ala Val Val
        355                 360                 365
Ala Val Leu Glu Ser Thr Leu Ser Cys Glu Ala Cys Lys Asn Gly Met
    370                 375                 380
Pro Thr Ile Ser Arg Leu Leu Gln Met Pro Leu Phe Ser Asp Val Leu
385                 390                 395                 400
Leu Thr Thr Ser Glu Lys Pro Gln Phe Lys Ile Pro Thr Lys Leu Lys
                405                 410                 415
Glu Ala Leu Arg Ile Ala Lys Cys Cys Ile Glu Lys Arg Leu Ile Glu
            420                 425                 430
Glu Gln Lys Gln Ile His Gln His Arg Arg Leu Thr Arg Ala Gln Ser
        435                 440                 445
His His Gly Ser Glu Glu Arg Lys Lys Arg Lys Ile Leu Ala Arg
    450                 455                 460
Lys Lys Ser Lys Arg Ser Ala Leu Glu Asn Ser Glu Glu His Ser Ala
465                 470                 475                 480
Lys Tyr Ser Asn Ser Asn Asn Ser Ala Gly Ser Gly Ala Ser Ser Pro
                485                 490                 495
Leu Thr Ser Pro Ser Ser Pro Thr Pro Pro Thr Ser Gly Ile Ser
            500                 505                 510
Ala Leu Pro Pro Pro Pro Pro Pro Pro Pro Ala Ala Pro Leu
        515                 520                 525
Pro Pro Ala Ser Thr Glu Ala Pro Ala Gln Leu Ser Ser Gln Ala Val
    530                 535                 540
Asn Gly Met Ser Arg Gly Ala Leu Leu Ser Ser Ile Gln Asn Phe Gln
545                 550                 555                 560
Lys Gly Thr Leu Arg Lys Ala Lys Thr Cys Asp His Ser Ala Pro Lys
                565                 570                 575
Ile Gly

<210> SEQ ID NO 8
<211> LENGTH: 1737
<212> TYPE: DNA
<213> ORGANISM: Human

<400> SEQUENCE: 8
atggccttca tggagaagcc gccagccggc aaggtgctgc tggacgacac ggtgccgctg    60
acagcagcca tcgaggcgag ccagagcctg cagtcccaca cggaatatat tattcgagtg   120
caaagaggaa tttctgtgga aaacagctgg cagattgtta aagatacag tgactttgat    180 ttgcttaaca cagcttaca gattgcaggc ctaagtctac ctcttcctcc caaaaaattg    240
attggtaaca tggatcgtga attcatagct gaaaggcaga aaggtcttca gaactatctc    300
aacgtgatca caacaaatca tatcttgtct aattgtgagc tggttaagaa gttttttagat   360 ccaaacaact attccgcaaa ctatactgag attgccttgc aacaggtttc catgttcttc    420
```

-continued

```
cgatcagaac caaagtggga ggtggtggaa cctttgaaag acataggttg gagaataagg      480
aagaaatatt tcttgatgaa gattaaaaat cagccaaagg aacggctagt gttaagctgg      540
gctgaccttg gcccagacaa gtatttgtca gataaagatt ttcagtgtct aatcaaactt      600
ctgccttctt gtttgcaccc ttacatctat cgggttacct tgccacagc taatgaatcc       660 tcagcgttgc ttattaggat gtttaacgaa agggaacat tgaaggatct gatctacaag       720
gcaaaaccaa aagacccatt tctaaagaag tactgcaacc ctaagaagat tcagggcctg      780
gaactccagc aaataaaaac atatggacgg caaatattag aggtactgaa gtttcttcat      840
gacaagggat tcccttatgg gcatcttcac gcctccaatg tgatgctcga tggggacact      900
tgtcggctgc tggaccttga gaattcctta ttgggcctgc cttccttcta ccgatcttat      960
ttttcacaat tcaggaaaat caatacattg gaaagtgtgg atgtccactg ctttggccac     1020
ttactgtatg aaatgactta tggacgaccg ccagactcgg tgcctgtgga ctccttccct     1080
cctgccccgt ccatggctgt ggtggccgtg ttggagtcta cgctgtcttg tgaagcctgt     1140
aaaaatggca tgcctaccat ctcccggctc ttacagatgc cattattcag cgatgtttta     1200
ctaaccactt ctgaaaaacc acagtttaag atccctacaa agttaaaaga ggcattgaga     1260
attgccaaag aatgtataga gaagagacta attgaggaac agaaacagat tcaccagcat     1320
cgaagactga caagagctca gtcccaccat ggatctgagg aggaaagaaa aaaagaaag     1380 attttagctc gaaagaagtc aaaacgatct gctcttgaaa atagtgaaga gcattcagcg     1440
aagtacagca actccaataa ttcagcagga tctggggcca gctcacctct cacgtccccg     1500
tcatcgccaa ctccaccctc tacatcaggg atatctgcat acctccacc tcctccacct      1560 ccaccaccac cagcagctcc cttgcctcct gcgagcaccg aggcacctgc ccagctctcg     1620
tctcaggctg tgaatggcat gagccgaggg gccttgctca gctccatcca gaatttccaa     1680
aaaggaactt tgaggaaagc caaaacctgt gatcacagtg ctccgaagat cggctga         1737
```

<210> SEQ ID NO 9
<211> LENGTH: 20
<212> TYPE: DNA
<213> ORGANISM: Human

<400> SEQUENCE: 9
atctacaagg caaaaccaaa                                                   20

<210> SEQ ID NO 10
<211> LENGTH: 20
<212> TYPE: DNA
<213> ORGANISM: Human

<400> SEQUENCE: 10
gaaattctgg atggaactga                                                   20

<210> SEQ ID NO 11
<211> LENGTH: 20
<212> TYPE: DNA
<213> ORGANISM: Human

<400> SEQUENCE: 11
ggtggccgta ttggagtcta                                                   20

<210> SEQ ID NO 12
<211> LENGTH: 20
<212> TYPE: DNA
<213> ORGANISM: Human

```
<400> SEQUENCE: 12
tgaagacagt cctgctgtgg                                              20

<210> SEQ ID NO 13
<211> LENGTH: 20
<212> TYPE: DNA
<213> ORGANISM: Human

<400> SEQUENCE: 13
ggtggccgta ttggagtcta                                              20

<210> SEQ ID NO 14
<211> LENGTH: 20
<212> TYPE: DNA
<213> ORGANISM: Human

<400> SEQUENCE: 14
gttcaaagtg gtgcatgctc                                              20

<210> SEQ ID NO 15
<211> LENGTH: 20
<212> TYPE: DNA
<213> ORGANISM: Human

<400> SEQUENCE: 15
ggtggccgta ttggagtcta                                              20

<210> SEQ ID NO 16
<211> LENGTH: 20
<212> TYPE: DNA
<213> ORGANISM: Human

<400> SEQUENCE: 16
tgaagacagt cctgctgtgg                                              20

<210> SEQ ID NO 17
<211> LENGTH: 20
<212> TYPE: DNA
<213> ORGANISM: Human

<400> SEQUENCE: 17
ggtggccgta ttggagtcta                                              20

<210> SEQ ID NO 18
<211> LENGTH: 20
<212> TYPE: DNA
<213> ORGANISM: Human

<400> SEQUENCE: 18
gttcaaagtg gtgcatgctc                                              20

<210> SEQ ID NO 19
<211> LENGTH: 20
<212> TYPE: DNA
<213> ORGANISM: Human

<400> SEQUENCE: 19
cacggcattg taaccaactg                                              20

<210> SEQ ID NO 20
<211> LENGTH: 20
<212> TYPE: DNA
<213> ORGANISM: Human
```

-continued

```
<400> SEQUENCE: 20
ctgggtcatc ttttcacggt                                           20
```

NUCLEIC ACIDS ENCODING PROTEINS FOR MODULATING NA,K-ATPASE

CROSS-REFERENCE TO RELATED APPLICATION

This application claims priority to U.S. provisional patent application Ser. No. 60/853,326 filed Aug. 24, 2006, incorporated herein by reference in its entirety.

FIELD OF INVENTION

This invention is directed to an isolated protein MONaKA and methods of its use. Specifically, the invention is directed to a protein that modulates the Na,K-ATPase and glutamate transporters, by binding to the b-subunit of the plasma membrane Na,K-ATPase (Na pump).

BACKGROUND OF THE INVENTION

The Na,K-ATPase is a ubiquitous plasma membrane ion transporter, in fact, the first enzyme recognized to be an ion pump. It uses the hydrolysis of one molecule of ATP to drive the coupled transport of three sodium ions out of the cell and two potassium ions into the cell. Its activity is essential for maintaining membrane ion gradients responsible for membrane potential by clearing potassium from the extracellular space and removing excess sodium from the intracellular space. Cardiac glycosides, such as ouabain and strophanthidin, which are used to treat some forms of cardiac disease, produce some or all of their effects by blocking the pumping activity of the Na,K-ATPase.

Na,K-ATPase is a member of the family of P-type ATPases. It is a heterodimeric integral membrane protein, consisting of one $\alpha$ and one $\beta$ subunit. The $\alpha$ subunit, an ~100 kDa protein with 10 predicted membrane spans, is the catalytic subunit responsible for ion translocation and ATPase activity. The $\beta$ subunit, a 50-60 kDa glycosylated protein with a single membrane-spanning domain, may act as a molecular chaperone or otherwise regulate the membrane targeting and/or function of the $\alpha$ subunit. At least four distinct $\alpha$ subunit and three $\beta$ subunit isoforms have been identified, and there appears to be no preferential association of particular $\alpha$ subunits with particular $\beta$ subunits.

Relatively little is known about the endogenous regulation of Na,K-ATPase. Catecholamines (Phillis, J. W., Cell, Tissue and Organ Cultures in Neurobiology, pp. 93-97 (1978); Horwitz, B. A., Fed. proc., 38:2170-2176 (1979)), thyroid hormone (Smith, T. J. and I. S. Edelman, Fed. Proc., 38:2150-2153 (1979)), aldosterone (Rossier, B. C., et al., Science, 12:483-487 (1987)), linoleic and linolenic acids (Bidard, J. N., et al., Biochem. Biophys. Acta., 769:245 (1984); Tamura, M., et al., J. Biol. Chem., 260:9672 (1985); and vanadium (Cantley, L. C., Jr., et al., J. Biol. Chem., 243:7361-7368 (1978)) have all been linked to either direct or indirect effects on enzyme activity.

There are several neurological diseases or disorders in which there has been reported a change in Na pump function, such as familial hemiplegic migraine, cardiac disease, end-stage kidney disease, neuropathy, and others. Therefore, a modulator of Na,K-ATPase is highly desirable for its potential as a drug for treating these disorders or diseases

SUMMARY OF THE INVENTION

In one embodiment, the invention provides an isolated nucleic acid which encodes a mammalian MONaKA protein, which modulates the Na,K-ATPase and glutamate transporters, said mammalian MONaKA protein comprises a nucleic acid sequence as set forth in SEQ ID NO. 2, 4, 6, or 8 including variants, and mutants, thereof.

In another embodiment, provided herein is a MONaKA polypeptide comprising the amino acid sequence of a mammalian MONaKA.

In one embodiment, provided herein is a method of modulating the activity of Na,K-ATPase in a cell, comprising contacting the cell with an effective amount of a MONaKA polypeptide, whereby said polypeptide binds to the beta subunit of the plasma membrane Na,K-ATPase, thereby modulating its activity.

In another embodiment, provided herein is a method of decreasing ion flux across a membrane in a cell, comprising contacting the cell with an effective amount of a MONaKA polypeptide, whereby said polypeptide binds to the beta subunit of the plasma membrane Na,K-ATPase, thereby modulating its activity resulting in reduced ion flux across the membrane.

In one embodiment, provided herein is a method of modulating glial glutamate transporters in a subject, comprising contacting glial cells with an effective amount of MONaKA polypeptide, thereby decreasing glutamate transport across the plasma membrane.

In another embodiment, provided herein is a method of treating acute epilepsy in a subject, comprising the step of administering to said subject an effective amount of an agent capable of inhibiting the expression or function of MONaKA polypeptide or it's encoding gene, whereby the MONaKA polypeptide is elevated at the acute stage of epilepsy.

In one embodiment, provided herein is a composition for the treatment of disorders or diseases associated with abnormal function of Na,K,ATPase comprising a MONaKA polypeptide, or an agent capable of inhibiting the expression or function of said MONaKA protein.

In one embodiment, provided herein is a peptide capable of mimicking a function of MONaKA polypeptide, wherein said function is decreasing glutamate transport across the plasma membrane, modulation of glial glutamate transport, modulation of Na,K,ATPase activity or a combination thereof.

BRIEF DESCRIPTION OF THE DRAWINGS

FIG. 3E, arrowhead), which shows the most intense staining in the CNS or peripheral nervous system. At higher magnification, axonal staining is seen in spinal cord white matter (FIG. 3B, arrows), dorsal root ganglion neurons (FIG. 3E, arrow), and sciatic nerve (FIG. 3F, arrowhead; FIG. 3G). Within the ventral horn of the spinal cord, cytoplasmic staining is seen in α-motoneurons (FIGS. 3A, 3C) with a lack of staining in the nucleus or nucleolus (FIG. 3C). A longitudinal section of sciatic nerve demonstrates Schwann cell immunoreactivity on the membrane of the Schwann cell but not within the myelin itself (FIG. 3F, arrow; FIG. 3G, arrow), as well as in sciatic nerve axons (FIG. 3F, arrowhead; FIG. 3G, arrowhead).

As shown in FIG. 4A, both hippocampal and cortical neurons (lanes 1-4) have an intense band for the short version of MONaKA (MO) and have full-length message as well, whereas astrocytes, oligodendrocytes, and microglia (lanes 5-10) show a more intense band for full-length than short MONaKA. The left lane shows molecular weight markers. The expected PCR product size is 439 bp for the full-length transcript and 450 bp for the short transcript. Lanes: 1, cortical neurons, full-length; 2, cortical neurons, short; 3, hippocampal neurons, full-length; 4, hippocampal neurons, short; 5, astrocytes, full-length; 6, astrocytes, short; 7, oligodendrocytes, full-length; 8, oligodendrocytes, short; 9, microglia, full-length; 10, microglia, short. FIG. 4B shows densitometric quantitation of the relative amounts of MONaKA mRNA. Each bar represents results from cultures prepared from 8-14 pooled animals, normalized to an internal β-actin standard (146 by band), and RT-PCR was performed three times to ensure reproducibility. Lane labeling is the same as in FIG. 4A.

FIG. 5A shows results from the yeast two-hybrid screen. Both the short and full-length MONaKA sequences were used as baits in yeast two-hybrid screens. Of 21 positive clones, nine encoded amino acids 120-258 of the β3 subunit of the Na,K-ATPase. The other 12 clones encoded a portion of the C-terminal domain of the β 1 subunit of the Na,K-ATPase, n indicates number of clones. As shown in FIG. 5B, mouse MONaKA (MO) coimmunoprecipitates with the β1 and β3 subunit C-terminal fragments identified in the yeast two-hybrid screen (23 and 22 kDa, respectively). tsA201 cells were transfected with either the short or full-length versions of HA-tagged MONaKA, together with Myc-tagged Na,KATPase β1 or β3 subunit C-terminal fragments. Identical results were obtained for β1 (left panels) and β3 (right panels) subunit fragments. Western blot demonstrates that the β3 subunit fragment expression (top panels) and immunoprecipitation (IP) (middle panels) are similar in the absence or presence of MONaKA. A β subunit fragment band is observed in the MONaKA immunoprecipitate (bottom panels) only when β subunit fragment and MONaKA are transfected together. No bands were seen when vector only was used as control.

FIG. 7A shows GST pull-down. Native b subunits of Na,K-ATPase can be pulled down from lysates of purified cultured astrocytes (left) or whole mouse brain crude membranes (right) by both the short (S) and full-length (FL) versions of GST-MONaKA (MO) but not by GST alone. As shown in FIG. 7B, immunoprecipitation (IP) with an anti-β subunit antibody of Na,K-ATPase can coimmunoprecipitate MONaKA from lysates of cultured astrocytes (top) or whole mouse brain crude membranes (bottom). As shown in FIG. 7C, the specificity of the antibodies used to immunoprecipitate and blot for the β1 and β3 subunits was confirmed by deglycosylation of brain membrane samples; the antibodies recognize both the glycosylated and deglycosylated forms of the native β1 (top panel) and β3 (bottom panel) subunits.

As shown in FIG. 8A, brain cytoplasmic and membrane fractions were analyzed by Western blot to determine the distribution of MONaKA (MO). MONaKA protein is found in both the brain cytoplasm and membrane fractions, with approximately two-thirds of the protein associated with the membrane based on densitometric analysis. As shown in FIG. 8B, cell surface biotinylation, tsA201 cells were transfected with Myc-Na,K-ATPase 131 subunit (lane 1) or HA-MONaKA (lane 2) or both together (lane 3). After surface biotinylation (see Materials and Methods in the Examples), both MONaKA and the b1 subunit (positive control) can be detected in avidin precipitates (bottom panels) using anti-HA or -Myc antibodies, respectively. The cytoplasmic protein Myc-14-3-3 is not present in the avidin precipitate under these experimental conditions (lane 4).

As shown in FIG. 9A, the production of inorganic phosphate from ATP by a partially purified Na,K-ATPase preparation was measured by a colorimetric assay. The ouabain-sensitive portion of the total ATPase activity was taken as the basal Na,K-ATPase activity (1.2 µl mol Pi/mg protein/min). This activity is inhibited by both short (S) and full-length (FL) GST-MONaKA (MO) but not by GST alone or GST-*Drosophila* Slob (data not shown) (*$p<0.05$, significantly different from control). Similar results were obtained with Na,K-ATPase from purified cultured astrocytes (data not shown). As shown in FIG. 9B, tsA201 cells were transfected with vector (Mock) with or without full-length MONaKA (left two lanes) or with α1β1 Na,K-ATPase subunits with or without full-length MONaKA (right two lanes). The ouabain-sensitive portion of total $^{86}$Rb$^+$ uptake was taken as that attributable to the Na,K-ATPase. Identical results were obtained with the short version of MONaKA (data not shown). Each data point is the mean SE of three experiments (*p<0.05, significantly different from transfection without MONaKA). Both endogenous and α1β1-mediated $^{86}$Rb$^+$ uptake are inhibited by MONaKA.

DETAILED DESCRIPTION OF THE INVENTION

Figure 1:
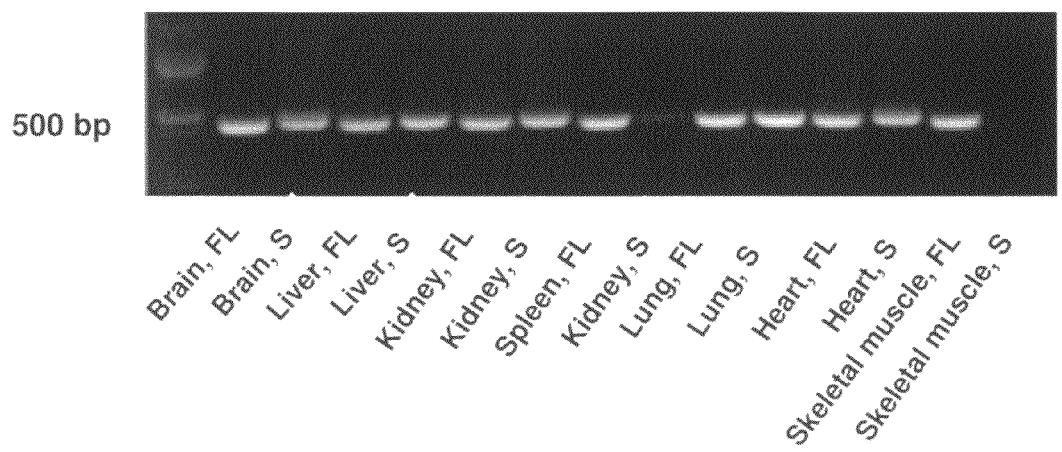
FIG. 1 shows MONaKA mRNA distribution in various mouse tissues. All tissues examined contain mRNA for the full-length (FL) version of the protein, as determined by RT-PCR. The short (S) version is also found in most tissues, with a low amount in spleen and none in skeletal muscle.FL product size, 439 bp; S product size, 450 bp. RT-PCR was performed three times in different animals with similar results.

This invention relates in one embodiment to an isolated protein MONaKA and methods of its use. Specifically, the invention is directed to a protein that modulates the Na,K-ATPase and glutamate transporters, by binding to the b-subunit of the plasma membrane Na,K-ATPase (Na pump).

In one embodiment, MONaKA exists in at least two splice variants, and the splicing is conserved between mouse and human. In one embodiment, the protein contains a putative protein kinase domain in its central region that is most similar to *Drosophila* Slob. In another embodiment, MONaKA contains a PX motif of the sort that has been shown to bind phoshoinositides. In one embodiment, the MONaKA sequence contain multiple proline residues organized in polyproline motifs, most notably in the C-terminal domain. Such motifs often participate in protein-protein interactions. Of particular interest is the fact that the longest polyproline motif is present only in the full-length splice variant of MONaKA (SEQ ID NO. 3 and 7). The expression of both splice variants is widespread throughout the CNS and peripheral nervous system, in neurons and glia, but the relative amount of the two splice variants varies from one cell type to another. In another embodiment glial cells of various types tend to express more full-length than short MONaKA, whereas the opposite is true for neurons. The functional significance of this differential expression of the splice variants remains to be determined.

In one embodiment therefore, provided herein is an isolated nucleic acid which encodes a mammalian MONaKA protein, which modulates the Na,K-ATPase and glutamate transporters, said mammalian MONaKA protein comprises a nucleic acid sequence as set forth in SEQ ID NO. 2, 4, 6, or 8 including variants, and mutants, thereof. In one embodiment, the nucleic acid used in the methods and compositions described herein, has a nucleic acid sequence having 75-99% similarity with the nucleic acid coding the sequence of SEQ ID NOs: 2, 4, 6, or 8. In one embodiment, the nucleic acid is a DNA or RNA, or cDNA or genomic DNA in other embodiments.

A surprise was the finding that MONaKA appears to be tightly associated with the plasma membrane, even under conditions that should dissociate it from any of its binding partners. The presence of a PX-like phosphoinositide binding motif in the MONaKA sequence is consistent with membrane association but cannot account for the surface biotinylation results. Although there are no predicted membrane spanning domains in the MONaKA sequence, the biotinylation data shows that at least a portion of the protein is outside the plasma membrane. The C-terminal portion of the Na,K-ATPase $^3$subunits, to which MONaKA binds, is also thought to be extracellular (Crambert and Geering, 2003↓). In one embodiment, MONaKA is secreted from neurons or glia, via an exocytotic mechanism in another embodiment.

In one embodiment, provided herein, is an oligonucleotide of at least 15 nucleotides, or an antisense molecule in another embodiment, which capable of specifically hybridizing with a sequence of the nucleic acid, such as DNA or RNA in certain embodiments, which encodes the mammalian MONaKA described herein, which is used in the methods and compositions described herein. In another embodiment, provided herein is a nucleic acid having a sequence complementary to the sequence of the isolated nucleic which encodes a mammalian MONaKA protein, which modulates the Na,K-ATPase and glutamate transporters, said mammalian MONaKA protein comprises a nucleic acid sequence as set forth in SEQ ID NO. 2, 4, 6, or 8 including variants, and mutants, thereof.

In another embodiment, Provided herein is a vector comprising isolated nucleic acid which encodes a mammalian MONaKA protein, which modulates the Na,K-ATPase and glutamate transporters, said mammalian MONaKA protein comprises a nucleic acid sequence as set forth in SEQ ID NO. 2, 4, 6, or 8 including variants, and mutants, thereof. In one embodiment, the vector further comprising a promoter such as a bacterial, yeast, insect or mammalian promoter in certain embodiments, of RNA transcription, or an expression element operatively linked to the nucleic acid, wherein the vector is in one embodiment a plasmid, or cosmid, yeast artificial chromosome (YAC), BAC, adenovirus, adeno-associated virus, retrovirus, P1, bacteriophage or eukaryotic viral DNA in other embodiments.

In one embodiment, provided herein is a MONaKA polypeptide comprising the amino acid sequence of a mammalian MONaKA, such as the amino acid sequence is set forth in SEQ ID NOs: 1, 3, 5, or 7. In one embodiment, provided herein is a antibody wherein the antibody is a monoclonal or polyclonal antibody, or a functional fragment thereof, such as Fab, Fab' Fc and the like n other embodiments, which specifically binds to a MONaKA polypeptide comprising the amino acid sequence of a mammalian MONaKA, such as the amino acid sequence is set forth in SEQ ID NOs: 1, 3, 5, or 7.

Most interesting is that MONaKA can modulate the ATPase and ion transport activities of the Na,K-ATPase. The ATPase activity from whole brain or cultured astrocytes is inhibited by the addition of exogenous MONaKA, suggesting that in certain embodiments, the Na,K-ATPase is not fully saturated with endogenous MONaKA in these cells. According to this aspect and in one embodiment, provided herein is a method of modulating the activity of Na,K-ATPase in a cell, comprising contacting the cell with an effective amount of a MONaKA polypeptide, whereby said polypeptide binds to the beta subunit of the plasma membrane Na,K-ATPase, thereby modulating its activity. In one embodiment, the MONaKA polypeptide its amino acid sequences and its encoding nucleotide sequences, or a functional derivative, analog or mutant or a combination thereof; are used in the methods described herein. In another embodiment, provided herein is a method of decreasing ion flux across a membrane in a cell, comprising contacting the cell with an effective amount of a MONaKA polypeptide, whereby said polypeptide binds to the beta subunit of the plasma membrane Na,K-ATPase, thereby modulating its activity resulting in reduced ion flux across the membrane, wherein in other embodiments, the ion is Na+, K+ or a combination thereof.

Prolonged or intense neuronal firing can lead to the accumulation of extracellular potassium ions and the disruption of the normal plasma membrane ion gradients. Elevated extracellular potassium, in turn, can cause membrane depolarization, leading to excitotoxicity as a result of the excessive release of the neurotransmitter glutamate from astrocytes or synaptic terminals. Because potassium accumulates to high concentrations in the relatively restricted extracellular space bounded by the presynaptic and postsynaptic neuronal elements and the associated astrocyte, this may be a particularly acute problem at CNS synapses. In one embodiment, it is particularly interesting that MONaKA is expressed at high levels in astrocytes (as well as other glial cells) and modulates the astrocyte Na,K-ATPase. Therefore, in one embodiment provided herein is a method of decreasing ion flux across a membrane in a cell, comprising contacting the cell with an effective amount of a MONaKA polypeptide, whereby said polypeptide binds to the beta subunit of the plasma membrane Na,K-ATPase, thereby modulating its activity resulting in reduced ion flux across the membrane.

An additional role for the astrocyte Na,K-ATPase at the synapse is to help with the uptake of neurotransmitter released into the synaptic cleft. The glutamate transporters responsible for uptake into astrocytes are powered by the plasma membrane sodium gradient and mediate the coupled transport of sodium and glutamate into the cell. The resulting elevated intracellular sodium activates the Na,K-ATPase, resulting in the restoration of the normal ionic gradients. Interestingly, the two major astrocyte sodium-dependent glutamate transporters are tightly colocalized with the Na,K-ATPase in perisynaptic regions. Consistent with this close association is the finding that glutamate uptake by cultured astrocytes stimulates Na,K-ATPase activity, possibly by the recruitment of a specific isoform that is mobilized in response to synaptic activity. Therefore, provided herein is a method of modulating glial glutamate transporters in a subject, comprising contacting glial cells with an effective amount of MONaKA polypeptide, thereby decreasing glutamate transport across the plasma membrane.

In one embodiment, results using three different animal models that mimic epilepsy show that MONaKA protein increases in brain during the acute phase of epilepsy, but returns to baseline during the chronic phase. This result indicates that pharmacologically targeting MONaKA or its binding site on the beta subunit prevent in one embodiment epilepsy or other diseases/disorders that show abnormalities in Na pump activity. Accordingly provided herein is a method of treating acute epilepsy in a subject, comprising the step of administering to said subject an effective amount of an agent capable of inhibiting the expression or function of MONaKA polypeptide or it's encoding gene, whereby the MONaKA polypeptide is elevated at the acute stage of epilepsy. In one embodiment, that agent is an antibody, a siRNA, a virus, polyamides, triple-helix-forming agents, antisense RNA, synthetic peptide nucleic acids (PNAs), agRNA, LNA/DNA copolymers, small molecule chemical compounds, or a combination thereof; and inhibiting the expression or function of MONaKA polypeptide or it's encoding gene, comprises lowering the level of a protein or nucleic acid regulating the expression or function of said MONaKA gene, or inhibiting function of MONaKA polypeptide.

In one embodiment, the term "treatment", or "treating" refers to any process, action, application, therapy, or the like, wherein a subject, including a human being, is subjected to medical aid with the object of improving the subject's condition, directly or indirectly. The term "treating" refers also to reducing incidence, or alleviating symptoms, eliminating recurrence, preventing recurrence, preventing incidence, improving symptoms, improving prognosis or combination thereof in other embodiments. "Treating" embraces in another embodiment, the amelioration of an existing condition. The skilled artisan would understand that treatment does not necessarily result in the complete absence or removal of symptoms.

In one embodiment, the term "siRNA" refers to RNA interference, which in another embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response.

In one embodiment, the term "conserved", refers to amino acid sequences comprising the peptides or nucleotides described herein, which remain in one embodiment, essentially unchanged throughout evolution, and exhibit homology among various species producing the protein.

The presence of long dsRNAs in cells stimulates in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence. The consequence of these events, in one embodiment, is the inhibition of gene expression.

In another embodiment, "complementarity" indicates that the oligonucleotide has a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the term "TFO" or "triplex forming oligonucleotide" refers to the synthetic oligonucleotides of the present invention which are capable of forming a triple helix by binding in the major groove with a duplex DNA structure.

In another embodiment, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods described herein, without changing the scope of the invention.

The term "nucleic acid" as used in connection with siRNA, refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like. In one embodiment, the siRNAs used in the compositions and methods of the invention, are nucleic acid sequences.

In one embodiment, specific nucleic acids are targeted for antisense. "Targeting" an antisense compound to a particular nucleic acid, in one embodiment, is a multistep process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent.

In one embodiment, the methods described hereinabove, utilize the compositions described herein. In another embodiment, provided herein is a composition for the treatment of disorders or diseases associated with abnormal function of Na,K,ATPase comprising a MONaKA polypeptide, or an agent capable of inhibiting the expression or function of said MONaKA protein. In one embodiment, the MONaKA comprises an amino acid sequence as set forth in SEQ ID NOs: 1, 3, 5, 7, or a functional derivative, analog or mutant or a combination thereof. In one embodiment, the disease or disorder sought to be treated using the methods and compositions provided herein, is familial hemiplegic migraine, cardiac disease, end-stage kidney disease, neuropathy, epilepsy or a combination thereof.

In one embodiment, provided herein is a peptide capable of mimicking a function of MONaKA polypeptide, wherein said function is decreasing glutamate transport across the plasma membrane, modulation of glial glutamate transport, modulation of Na,K,ATPase activity or a combination thereof. In one embodiment, the peptide is a functional derivative, analog or mutant of any of SEQ ID NOS. 1-8.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Cloning of MONaKA

Mouse MONaKA cDNAs were amplified by PCR from a mouse brain cDNA library (Marathon-ready cDNA library; Clontech, Palo Alto, Calif.), using primers designed according to the sequence of GenBank accession number AK048910 [GenBank], which resembles Drosophila slob: 5' primer, 5'-gcccgggatggccttcatggagaa-3'; 3' primer, 5'-tcagccgatcttgggagcgctgtg-3'. Human MONaKA cDNAs were cloned using rapid amplification of cDNA ends (RACE) (Frohman, 1993↓). The template was a human brain cDNA library designed for RACE (Clontech). 3' RACE was performed using the outer gene-specific primer 5'-tggcatgcctaccatctccg-gctcttaca-3' and inner gene-specific primer 5'-cagtcccaccatg-gatctgaggaggaaaga-3'. 5' RACE was performed using the outer gene-specific primer 5'-cagcccagcttaacactagccgttcc-3' and inner gene-specific primer 5'-tatttcttccttattctccaacctatgtc-3'. The RACE products and the PCR products were sequenced and cloned into the mammalian expression vectors pcDNA3.1/V5/His-TOPO (Invitrogen, Carlsbad, Calif.) and PCMV-HA and pCMV-Myc (Clontech) to add either a hemagglutinin (HA) or a Myc epitope tag at the N terminus. The mouse MONaKA sequences (mMONaKA-S and mMONaKA-FL) have been deposited in GenBank with accession numbers DQ095196 [GenBank] (short) and DQ095197 [GenBank] (full-length). The human sequences (hMONaKA-S and hMONaKA-FL) have been deposited in GenBank with accession numbers DQ124708 [GenBank] (short) and DQ124707 [GenBank] (full-length).

Glutathione S-Transferase-MONaKA Fusion Proteins cDNAs encoding short and full-length MONaKA were fused to glutathione S-transferase (GST) in the pGEX-4T-1 vector and expressed in Escherichia coli BL21(DE3). pGEX-4T-1 with no insert was used as a control. Bacterial cultures containing the appropriate vectors were grown to a density of $A_{600}$=0.6-0.9, induced with 1 mM isopropylthiogalactoside, and shaken for an additional 4 h. The induced bacterial cultures were pelleted, resuspended in PBS with 1 mM DTT, 1 mM EDTA, and protease inhibitors [1 mM phenylmethylsulfonyl fluoride (PMSF) plus 1 μg/ml each aprotinin, leupeptin, and pepstatin A], and then lysed by sonication. Triton X-100 (1%) was added, and the lysate was incubated with rotation for 30 min at 4° C., followed by centrifugation at 12,000×g for 15 min at 4° C. Purification of the fusion protein was performed by adding a 50% slurry of glutathione-Sepharose 4B beads in PBS (1 μl/ml original culture volume) (Amersham Biosciences, Piscataway, N.J.) for 1 h at 4° C. with rotation. The beads were washed five times with PBS. GST fusion proteins were eluted with reduced glutathione elution buffer containing 50 mM Tris-HCl and 10 mM reduced glutathione (Sigma, St. Louis, Mo.), pH 8.0. Alternatively, the protein was retained on the washed beads and diluted to a bead/PBS slurry of 50%. Aliquots of the eluted protein or protein beads were frozen at −80° C. until use.

Antibody Preparation

An MONaKA antibody that recognizes both the full-length and short versions of the protein was generated by immunizing rabbits with a GST fusion protein containing amino acids 229-291 of mouse MONaKA. This sequence was cloned into the pGEX4T-1 and pMAL-β2X vectors (Amersham Biosciences, Piscataway, N.J.). The maltose (pMAL) fusion protein was purified with amylose beads (New England Biolabs, Beverly, Mass.). The immunized rabbit serum was first passed through a GST column to remove antibodies that recognized GST and then purified with pMAL-MONaKA-conjugated beads.

Reverse Transcription-PCR Tissue Distribution of MONaKA.

Whole RNA was extracted from mouse brain, liver, kidney, spleen, lung, heart, and skeletal muscle using Ultraspec RNA Isolation System (Biotex, Houston, Tex.), precipitated with an equal volume of isopropanol, and washed with 75% ethanol. Two to 2.5 µg of total RNA were reverse transcribed into cDNA using oligo-dT primers (Superscript First-Strand Synthesis System for RT-PCR; Invitrogen). Outside primers that crossed the 11-12 intron/exon border to prevent amplification of contaminating genomic DNA were used initially to amplify cDNA (5'-ATCTACAAGGCAAAACCAAA-3' (SEQ ID NO. 9) and 5'-GAAATTCTGGATGGAACTGA-3' (SEQ ID NO. 10)). PCR amplification of the outside primer product was performed using inside primers specific for either the full-length or short version of MONaKA. For full-length, the 5' primer was 5'-GGTGGCCGTATTG-GAGTCTA-3' (SEQ ID NO. 11), and the 3' primer was 5'-TGAAGACAGTCCTGCTGTGG-3' (SEQ ID NO. 12). For the short version, the 5' primer was 5'-GGTGGCCGTAT-TGGAGTCTA-3', and the 3' primer was 5'-GTTCAAAGTG-GTGCATGCTC-3' (SEQ ID NO. 14). PCR was repeated three times to confirm the results.

Immunohistochemistry

Immunostaining was performed on 4% paraformaldehyde-perfused mouse tissue. Briefly, frozen, cryoprotected 20 µm sections were cut from brain, spinal cord, dorsal root ganglion, and sciatic nerve and floated in PBS. Sections were blocked with 10% normal goat serum in PBS with 0.1% Triton X-100 (PBS-T) and incubated overnight with primary antibody. Sections were rinsed in PBS-T, processed using rabbit Vectastain Elite ABC kit (Vector Laboratories, Burlingame, Calif.), and developed with 0.5 mg/ml 3,3'-diaminobenzidine tetrahydrochloride in PBS. Controls included preabsorbed antibody, preimmune serum, and no primary, secondary, or avidin-HRP.

Purified Cell Cultures

Primary hippocampal and cortical cultures were prepared from embryonic rat pups as described previously and plated on poly-L-lysine-coated plates with Neurobasal medium (Invitrogen). Cultures were allowed to grow for 5 d before harvesting for reverse transcription (RT)-PCR (see below). Purified rat oligodendrocyte cultures were prepared. Final purification of the cultures was done by immunopanning, which created a 94% pure oligodendrocyte culture (the remaining 6% were GFAP-positive astrocytes). Schwann cell cultures were prepared as described previously. The cultures were 95% pure, as determined by staining with p75, which specifically labels Schwann cells. Cortical astrocyte and microglial cultures were made using embryonic mouse pups. After 7 d, flasks containing astrocytes and microglia were shaken on a horizontal clinical rotator at 260 rpm for 90 min. Microglia are loosened during this process and float into the supernatant. The supernatant containing the microglia was collected and plated into a separate flask and allowed to incubate for 1 h at 37° C. in a humidified $CO_2$ chamber. After 1 h, the medium was replaced with fresh DMEM, supplemented with 10% fetal bovine serum and penicillin and streptomycin (100 U/ml), and allowed to grow for 24 h before harvesting. Astrocyte cultures were harvested immediately after shaking. Both cultures were determined to be 98% pure by immunostaining with anti-GFAP (G-3898; Sigma), *Griffonia simplicifolia* lectin I isolectin B4 (L-3759; Sigma), and anti-CNPase (C5922; Sigma).

Semiquantitative RT-PCR

Semiquantitative RT-PCR was performed on cultured rat cortical and hippocampal neurons, oligodendrocytes, and Schwann cells, as well as mouse astrocytes and microglia. RNA was extracted and reverse transcribed as described above. PCR amplification was performed using primers specific for either the full-length or short version of MONaKA. For full-length, the 5' primer was 5'-ggtggccgtattggagtcta-3' (SEQ ID NO. 15), and the 3' primer was 5'-tgaagacagtcctgct-gtgg-3' (SEQ ID NO. 16). For the short version, the 5' primer was 5'-ggtggccgtattggagtcta-3' (SEQ ID NO. 17), and the 3' primer was 5'-gttcaaagtggtgcatgctc-3' (SEQ ID NO. 18). Semiquantification of the PCR product was as described previously (Kendall et al., 1996↓) with minor modifications. Briefly, cDNA amplification of MONaKA and β-actin (5' primer, 5'-cacggcattgtaaccaactg-3'; 3' primer (SEQ ID NO. 19), 5'-ctgggtcatcttttcacggt-3' (SEQ ID NO. 20)) was performed in the same tube for each of the samples to eliminate between-sample variation and was tested to ensure that samples were in the linear phase of amplification. To test for genomic DNA contamination, MONaKA genomic primers were used as controls. Additional RT-PCR controls included primers for glial fibrillary acidic protein and neuron-specific enolase to ensure the purity of the different cultures. The semiquantitative RT-PCR was performed three times with similar results.

Yeast Two-Hybrid Screen

The yeast two-hybrid screen was performed using MATCHMAKER System 3 (Clontech). Briefly, the entire coding sequence of the short form or full-length MONaKA from mouse were cloned into bait vector, pGBKT7, and transformed into yeast strain AH109. The baits were screened against a mouse brain cDNA library and a mouse embryo cDNA library, which were pretransformed into yeast Y187 cells. Approximately 3,000,000 mating yeast colonies were screened for MONaKA-interacting proteins. Positive clones were selected on plates lacking adenine, histidine, leucine, and tryptophan and were assayed for galactosidase activity. The plasmids of true positive clones were isolated from yeast cells, and the sequences of the cDNAs were determined. To confirm the phenotype, true positive clones were retested by cotransforming baits and library plasmids into yeast cells.

Na,K-ATPase cDNA Constructs

Based on the yeast two-hybrid data, two cDNA constructs were created from the C terminus of mouse Na,K-ATPase β1 (amino acids 110-273) and β3 (amino acids 120-258). Each of these constructs was cloned into pCMV-Myc (Clontech), with the Myc tag located at the N terminus. These constructs were used for coimmunoprecipitation and Western blot when indicated. In addition, a full-length cDNA construct of mouse Na,K-ATPase β1 subunit was amplified by PCR from a mouse brain cDNA library. The primers, designed according to the sequence of mouse Na,K-ATPase β1 (GenBank accession number AK005071), were as follows: 5'-atggcccgcg-gaaaagccaaggaggaaggca-3' (SEQ ID NO. 19) and 5'-gat-cagctcttaatttcaatttttacatcaaag-3' (SEQ ID NO. 20). The cDNA was cloned into pCMV-Myc and pCMV-HA (Clontech), with the tags placed at the N terminus. The construct was sequenced through the entire coding region (DNA sequencing facility, University of Pennsylvania, Philadelphia, Pa.). Full-length rat Na,K-ATPase α1, α2, and α3 cDNAs (ouabain sensitive) were kindly provided by Drs. Amy Moseley, Adam Redden and Jerry B. Lingrel (University of Cincinnati, Cincinnati Ohio) and Thomas A. Pressley (Texas Tech University Health Sciences Center, Lubbock, Tex.).

Coimmunoprecipitation and Western Blotting tsA201 cells, derived from HEK293 cells and characterized by Margolskee et al. (1993↓), were grown in minimal essential medium supplemented with 10% fetal bovine serum and penicillin and streptomycin (100 U/ml). At ~40-50% confluency, cells were transfected with appropriate plasmids or vector only control using a calcium phosphate protocol. After 24 h, the medium was replaced with fresh supplemented medium. After an additional 24 h, the cells were washed three times in ice-cold PBS, pelleted at 3000×g at 4° C., and resuspended in buffer containing 1% 3-[(3-cholamidopropyl)dimethylaminonio]-1-propanesulfonate and 20 mM Tris-HCl, pH 7.5, 1 mM EDTA, 120 mM NaCl, 50 mM KCl, 50 mM NaF, 2 mM DTT, and protease inhibitors (1 mM phenylmethylsulfonyl fluoride plus 1 µg/ml each aprotinin, leupeptin, and pepstatin A). The resuspended cells were incubated for 30 min at 4° C. to allow solubilization. At the end of the incubation period, the lysates were spun down at 14,000×g in a tabletop microcentrifuge at 4° C. The supernatant was removed and used for immunoprecipitation. Lysates from confluent purified astrocyte cultures were prepared in the same way.

Immunoprecipitation was performed by preclearing the lysate with protein A/G PLUS-Agarose beads (Santa Cruz Biotechnology, Santa Cruz, Calif.) for 2 h at 4° C. The beads were removed by centrifugation at 3000×g for 5 min, and an aliquot of lysate was removed to confirm protein expression by Western blot (positive control). Proteins were immunoprecipitated from lysates by preincubating the precleared lysates with appropriate antibodies for 1 h before adding the protein A/G beads. The entire mixture was incubated overnight at 4° C. with rotation. The next day, the beads were rinsed three times with PBS, and the protein was eluted with 2× loading buffer. Precleared lysates or immunoprecipitates were then subjected to 4-15% gradient SDS-PAGE (Bio-Rad, Hercules, Calif.).

After SDS-PAGE, proteins were transferred to nitrocellulose membranes (Bio-Rad). The membranes were blocked with 5% nonfat milk in TBST (10 mM Tris-HCl, pH 7.5, 150 mm NaCl, and 0.1% Tween 20) and then incubated with appropriate primary antibodies in blocking buffer at 4° C. overnight (see below). After three washes with TBST, the blots were incubated with horseradish peroxidase-conjugated anti-mouse or anti-rabbit IgG (anti-mouse NA931 and anti-rabbit NA934; Amersham Biosciences, Arlington Heights, Ill.) for 1 h at room temperature. Proteins were detected with an enhanced ECL Western blotting detection reagent (Amersham Biosciences, Arlington Heights, Ill.). Molecular Analyst software (Bio-Rad) was used to quantify Western films.

Antibodies used for Western blot and coimmunoprecipitation were purchased from Upstate Biotechnology (Lake Placid, N.Y.; anti-Na,K-ATPase β1 06-170, β3 06-817, and α1 05-369), Sigma (anti-Myc M5546, anti-HA H9658, and anti-GST A7340), and Invitrogen (anti-V5 SC 138).

Mouse Brain Membrane Preparation

Mice were anesthetized and decapitated, and brains were immediately removed and snap frozen in liquid nitrogen. Individual brains were pulverized and then homogenized in a buffer containing 2.5 mM KCl, 250 mM sucrose, and 25 mM HEPES, pH 7.4, protease inhibitors (1 mM PMSF plus 1 µg/ml each aprotinin, leupeptin, and pepstatin A), and 2 mM DTT. The homogenate was centrifuged at 1000×g for 10 min to remove excess debris. The supernatant was removed and centrifuged for 1 h at 150,000×g. After this centrifugation, the supernatant was collected as the cytoplasmic fraction and the pellet as the crude membranes. The pellet was washed with the same buffer and centrifuged again for 1 h at 150,000×g. After the second centrifugation, the membrane pellet was resuspended in a buffer containing 1% Triton X-100, 20 mM Tris-HCl, pH 7.5, 10 mM EDTA, 120 mM NaCl, 50 mM KCl, 50 mM NaF, protease inhibitors, and 2 mM DTT to the same final volume as the cytoplasmic fraction.

GST-MONaKA Pull-Down of Na, K-ATPase βSubunits from Native Cells and Tissue.

A total of 0.5 µg (500 µl) of crude mouse brain membranes or purified cultured astrocyte lysates were incubated with 50 µl of a 50% slurry of GST or GST-MONaKA beads at 4° C. for 2 h (n=3). The beads were washed with PBS five times, resuspended in 2×SDS loading buffer, and subjected to 4-15% gradient SDS-PAGE. Na,K-ATPase β1 and β3 subunits were detected by Western blot.

Deglycosylation

Mouse brain membranes were prepared as described above, and proteins were deglycosylated using peptide N-glycosidase F (PNGase F; New England Biolabs), following the protocol provided with the enzyme and buffers. Briefly, a 25 µg sample of the membrane preparation was denatured in 50 µl of glycoprotein denaturing buffer (final concentration of 0.5% SDS with 1% β-mercaptoethanol) at 100° C. for 10 min, followed by the addition of a final concentration of 50 mM sodium phosphate buffer, pH 7.5, 1% NP-40, and 150 U of PNGase. The entire reaction mixture was incubated for 2 h at 37° C. and separated by SDS-PAGE. Western blots were developed as described above, using Na,K-ATPase β1 or β3 antibodies (Upstate Biotechnology).

Cell Surface Biotinylation

Cell surface biotinylation was performed as described previously (Wen and Levitan, 2002↓). Briefly, tsA201 cells were transfected with either HA-MONaKA alone or Myc-Na,K-ATPase β1 subunit alone or were cotransfected with HA-MONaKA and Myc-β1 subunit together. Forty-eight hours later, the cells were washed three times with PBS and incubated with 2 ml of 0.5 mg/ml Sulfo-NHS-LC-Biotin (Pierce; Rockford, Ill.) in PBS, pH 8.0, at room temperature for 30 min with gentle agitation. The biotin reagent was removed by washing the cells three times with PBS. Cells were harvested and resuspended in Western blot lysis buffer (described above) containing 20 µl of ImmunoPure immobilized streptavidin beads (Pierce) to isolate the biotinylated proteins. Protein in total cell lysates and streptavidin precipitates was detected by Western blotting with anti-HA and anti-Myc antibodies. Control cells were transfected with Myc-14-3-3, an intracellular protein that served as a negative control, as described previously. The experiment was repeated three times.

Preparation of Na,K-ATPase from Mouse Brain

Na,K-ATPase from mouse brain was prepared using a scaled-down protocol for the purification of Na,K-ATPase from rat brain (Mayrand et al., 1982↓). All steps, unless otherwise specified, were performed at 4° C. The meninges were removed from 25 mouse brains, and the brains were minced with scissors in medium A (0.25 M sucrose, 1 mM Tris-EDTA, and 10 mM imidazole-HCl, pH 7.7), homogenized with a tissue homogenizer at 6000 rpm, and centrifuged for 5 min in a Beckman Instruments (Fullerton, Calif.) J2-HC rotor at 1100×g, followed by a 20 min and then 5 min spin at 7700×g, each time retaining and recentrifuging the supernatant. The supernatant was centrifuged using a 50.2Ti rotor in a Beckman Instruments XL-90 Ultracentrifuge at 55,000×g for 30 min. The white membrane portion of the pellet was retained, discarding the brown pellet. The white membrane pellet was homogenized in medium A using six strokes in a Dounce homogenizer and then frozen at −20° C. until use.

Final purification of Na,K-ATPase was performed by thawing and continuously stirring the membrane preparation at 25° C. for 30 min with 3 mM ATP, 50 mM imidazole-HCl, pH 7.7, and 2 mM Tris-EDTA, with a protein (milligrams per milliliter) to SDS (milligrams per milliliter) ratio of 1.9. All subsequent centrifugation steps were performed with a 50.2Ti rotor in a Beckman Instruments XL-90 Ultracentrifuge. The resuspended membrane mixture was added to ice-cold medium B (2.1 M sucrose, 5 mM Tris-EDTA, and 20 mM imidazole-HCl, pH 7.7) and centrifuged at 250,000×g for 90 min. The floating protein band was removed and homogenized using six strokes of a Dounce homogenizer, resuspended in medium A, and centrifuged at 150,000×g for 45 min. The resulting pellet was resuspended in medium C (20% glycerol v/v, 5.4% sucrose w/v, 1 mM Tris-EDTA, and 25 mM imidazole-HCl, pH 7.4), homogenized with six strokes in a Dounce homogenizer, and centrifuged for an additional 150,000×g. The pellet was then resuspended and homogenized with a Dounce homogenizer in medium A plus 10% v/v glycerol and centrifuged at 150,000×g for 30 min. The final pellet was diluted to 1 mg/ml in medium A with 10% glycerol and stored at −20° C. until use. SDS-PAGE followed by Coomassie blue staining was performed to check for the appropriate size bands and the purity of the protein. All protein quantification was performed using a Bio-Rad Protein Assay kit, based on the method of Bradford (Bio-Rad).

ATPase Assay

The ATPase assay was performed based on a standard protocol (Jorgensen, 1988↓). GST fusion protein beads were washed with reaction buffer (130 mM NaCl, 20 mM KCl, 3 mM $MgCl_2$, and 25 mM imidazole-HCl, pH 7.5) three times to get rid of any residual PBS and resuspended to a 50% bead/buffer slurry. GST fusion protein bead slurry (10 µl) was preincubated for 10 min at 37° C. with 10 µl (10 µg) of semipurified Na,K-ATPase with the addition of 30 µl of reaction buffer. After the incubation, the entire 50 µl was transferred to test tubes containing 1 ml of prewarmed incubation buffer. Half of the samples included 5.0 mM ouabain. The reaction was initiated by the addition of 3 mM ATP, and the samples were incubated for 5 min at 37° C. The reaction was stopped with 1 ml of ice-cold 0.5 M HCl containing 170 mM ascorbic acid, 4 mM ammonium heptamolybdate, and 1% SDS, on ice. For color development, 1.5 ml of a solution containing 150 mM sodium metaarsenite, 70 mM sodium citrate, and 2% acetic acid was added, and the tubes were incubated at 37° C. for 10 min. The tubes were centrifuged at 3500×g for 5 min to concentrate the beads at the bottom. A 1 ml aliquot was taken from the tubes and transferred to disposable cuvettes for analysis. The absorbance was read at 850 nm. Alternatively, eluted GST fusion protein was used in the assay, and the assay was performed in a similar manner as with the beads with similar results. Controls included GST-dSlob, no membrane, washed and unbound glutathione-Sepharose beads, GST only, Na,K-ATPase without ATP, and all assay components added with stop buffer on ice to determine baseline inorganic phosphate levels. All assays were performed in triplicate. Statistical significance was assessed by a paired t test.

$^{86}Rb^+$ Uptake Assay $^{86}Rb^+$ uptake was measured by standard methods (Munzer et al., 1994↓; Garty et al., 2002↓) with slight modification. tsA201 cells were transfected with vector with or without MONaKA, or with Na,K-ATPase α1β1 subunits with or without MONaKA, using a standard calcium phosphate protocol. Forty-eight hours later, the cells were washed twice with 10 ml of 140 mM NaCl, 5 mM KCl, 1 mM $MgCl_2$, 1 mM $CaCl_2$, 5 mM glucose, and 5 mM HEPES-Tris, pH 7.4, and resuspended into 1 ml with gentle pipetting. A 200 µl aliquot of the resuspension was removed for Western blot and protein concentration analysis. The remaining cells were split into four tubes, centrifuged at 3000×g, and resuspended in the buffer above, with the addition of 0.1 mM furosemide, 0.01 mM monensin, with or without 5 mM ouabain. The tubes were preincubated for 10 min at 37° C., and then 2.5 µCi of $^{86}RbCl$ (Amersham Biosciences, Piscataway, N.J.) diluted in buffer with furosemide, monensin, and/or ouabain, as above, was added to each tube for a final reaction mixture of 500 µl. After an additional 0-15 min at 37° C., the cells were placed on ice with the addition of 500 µl of ice-cold PBS containing 5 mM $BaCl_2$ to stop the reaction. The tubes were centrifuged at 3000×g and washed three times with cold PBS containing 5 mM $BaCl_2$. Cells were lysed with 500 µl of 1 M NaOH, and the radioactivity in the lysate was determined on a Wallac 1410 liquid scintillation counter (Amersham Biosciences, Piscataway, N.J.). Radioactivity was normalized to protein concentration, determined by Bio-Rad Protein Assay kit (Bio-Rad). The expression of the α and βsubunits and MONaKA was examined by Western blotting to confirm equivalent expression in each plate. Statistical significance was assessed by a paired t test.

Example 1

Sequence and Splice Variants of MONaKA

Mouse and human variants of MONaKA were cloned based on their sequence similarity to *Drosophila* Slob. Mouse and human MONaKA exhibit >90% amino acid sequence identity and >97% similarity to one another. They also are identical in all properties that we have tested, and so we will not distinguish between them here. MONaKA is most similar to *Drosophila* Slob in a central domain constituting approximately half of the protein but exhibits little similarity in the N- and C-terminal domains. There are at least two splice variants of MONaKA depending on the absence or presence of a 33 bp cassette This cassette contains a stop codon that produces a truncated form of the protein (515 amino acids in human; 514 amino acids in mouse). In the absence of this cassette, a 578 amino acid human protein (581 amino acids in mouse) that we call full-length MONaKA is produced. The alternative splicing is conserved perfectly between mouse and human MONaKAs.

A conserved domain search reveals that MONaKA contains a PX-like domain near its N terminus (amino acids 32-122), of the kind that might bind to phosphoinositides It also contains a putative protein kinase domain in the central portion of the protein (amino acids 198-349). This is the region in which MONaKA most closely resembles *Drosophila* Slob, and we found recently that *Drosophila* Slob exhibits protein kinase activity that can be modulated by the cAMP-dependent protein kinase. An examination of the MONaKA sequence also reveals an unusually large number of proline residues, often clustered together to form polyproline motifs. The longest of these polyproline motifs is absent from the short splice variant of MONaKA. The functional significance of these multiple proline residues remains to be determined.

Example 2

Distribution of MONaKA

Figure 2:
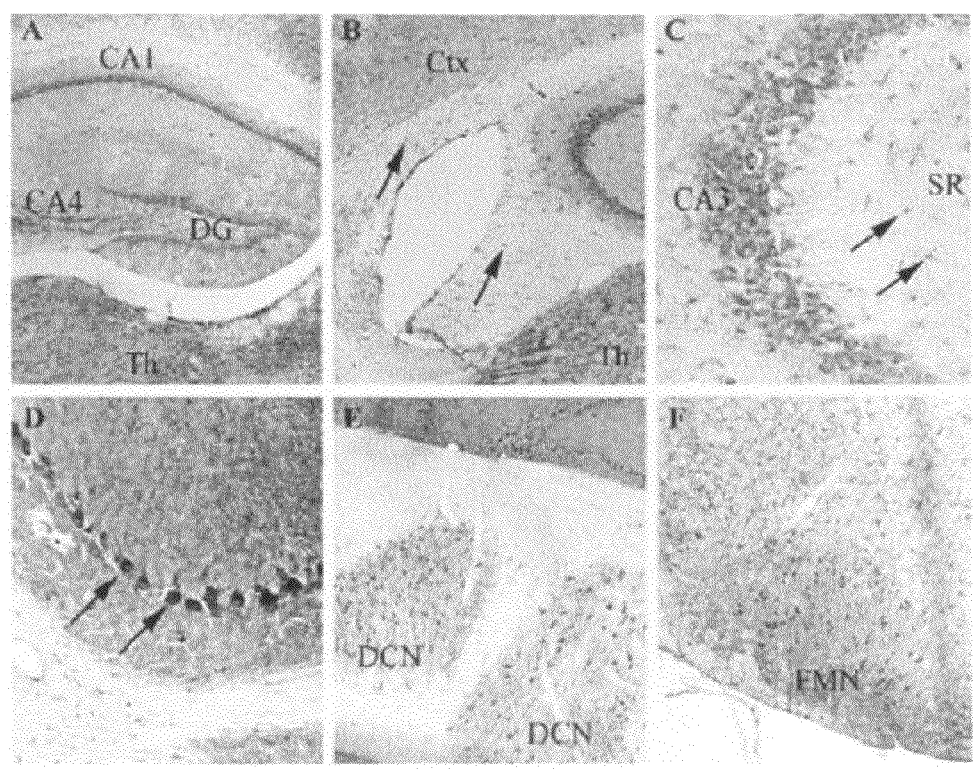
FIGS. 2A-2F show distribution of MONaKA in mouse brain. MONaKA immunostaining in the cortex and hippocampus (FIGS. 2A-2C), cerebellum (FIG. 2D, FIG. 2E), and brainstem (FIG. 2F). There is a widespread distribution of MONaKA protein within the cytoplasm of both neurons and glia. Immunopositive neurons are found in dentate gyms granule cells (DG), as well as in CA pyramidal cells of the hippocampal formation (FIG. 2A). At higher magnification (FIG. 2C), an example of the cytoplasmic distribution of MONaKA is seen within pyramidal cells of the CA3 region of the hippocampus. In addition, astrocytes within the stratum radiatum (SR) (FIG. 2C, arrows) are labeled. Thalamic (Th) and cortical (Ctx) neuronal staining is noted in all areas examined (FIG. 2A, FIG. 2B). Oligodendrocyte labeling is demonstrated by punctate staining in the fornix and corpus callosum (FIG. 2B, arrows). In the cerebellum, the most intense staining is found in the Purkinje cell bodies (FIG. 2D, arrows) and deep cerebellar nuclei (FIG. 2E, DCN), with less immunoreactivity present in the molecular and granule cell layers (FIG. 2D). In the brainstem (FIG. 2F), facial motor nucleus (FMN) neurons projecting out to the peripheral nervous system demonstrate strong cytoplasmic staining. Staining was performed three times in different animals with similar results.
Figure 3:
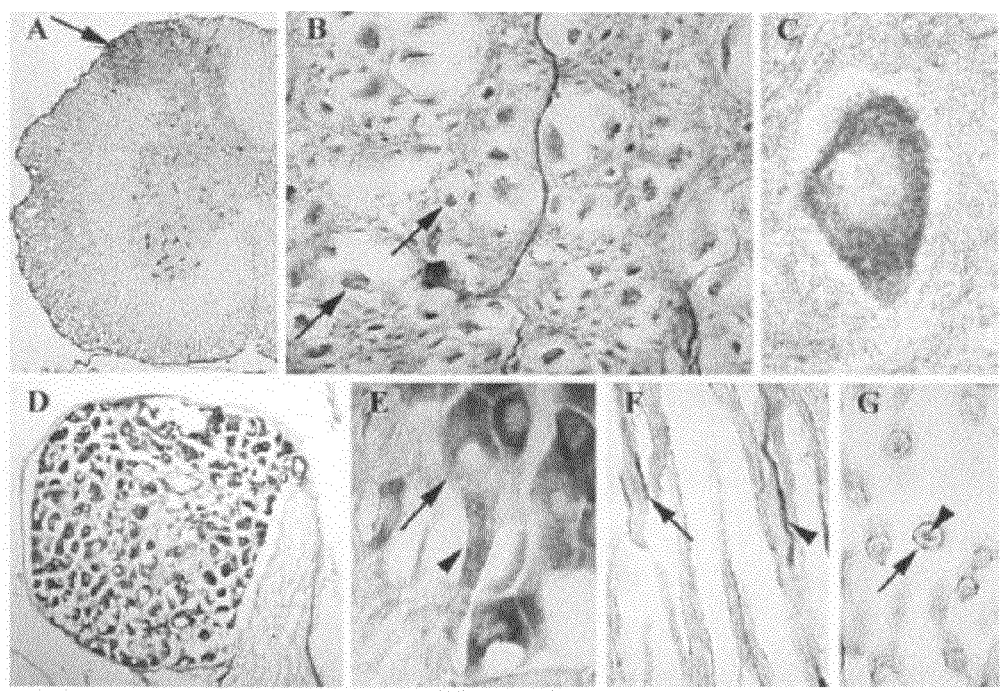
FIGS. 3A-G show distribution of MONaKA in mouse spinal cord and peripheral nervous system. In a low-magnification cross-section of lumbar spinal cord (FIG. 3A), note the intense staining in the dorsal root entry zone and superficial lamina (arrow). This staining is most likely in the axons of the dorsal root ganglion (FIG. 3D.

Using RT-PCR, we examined the mRNA distribution of both full-length and short MONaKA in various mouse tissues. mRNA for full-length MONaKA was found in all tissues examined, with the short form found in all tissues except skeletal muscle and very low levels in spleen (FIG. 1). Focusing on the nervous system, a polyclonal antibody that recognizes both splice variants of the protein was used and immunohistochemical techniques to verify MONaKA localization. MONaKA staining was found throughout the nervous system, in both neurons and glia (FIGS. 2, 3). Within neurons, staining is strong in the cytoplasm of the cell body and axon in both the CNS and peripheral nervous system. Staining in the CNS is seen in cortical and thalamic neurons, neurons of the hippocampal formation, cerebellum and brainstem (FIG. 2), and spinal cord αmotoneurons (FIG. 3A,C). The most intense immunoreactivity is observed in peripheral dorsal root ganglion neurons (FIG. 3D,E). FIG. 3E shows the clear cytoplasmic distribution of MONaKA in both the cell body and axon of a single dorsal root ganglion neuron. In fact, the axonal staining is so intense that the dorsal root entry zone and superficial lamina of the spinal cord are also strongly immunopositive (FIG. 3A).

Glial cells of the peripheral nervous system and CNS also demonstrate MONaKA immunoreactivity. Within the CNS, oligodendrocytes (FIG. 2B), astrocytes (FIG. 2C), and microglia (data not shown) all are immunopositive for MONaKA. In the peripheral nervous system, Schwann cells also express MONaKA (FIG. 3F,G); however, the expression pattern appears to be on the Schwann cell membrane, not within the myelin or, more interestingly, not at the nodes of Ranvier. This widespread expression pattern in both neurons and glia suggests that MONaKA may play an important role in the nervous system.

Example 3

Figure 4:
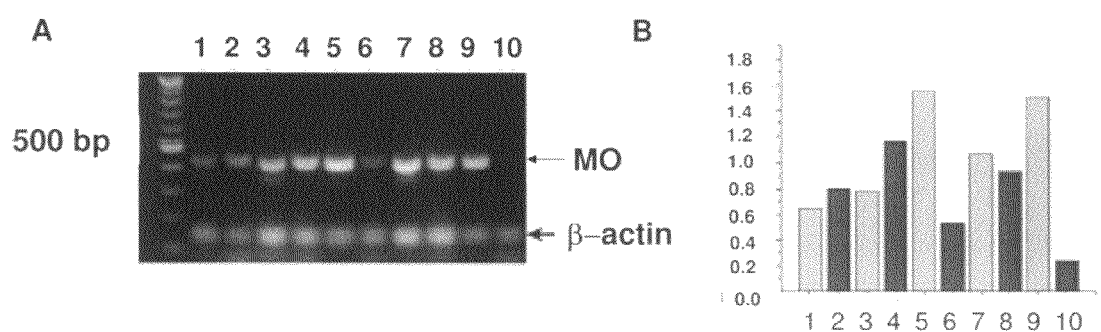
FIGS. 4A-B show semiquantitative RT-PCR analysis of MONaKA transcripts in cultured cells.

Differential Expression of Full-Length and Short Versions of MONaKA in Neurons and Glia Because the immunohistochemical staining could not differentiate between the short and full-length versions of MONaKA, we performed semiquantitative RT-PCR on purified cultured cells with primers specific to each splice variant. Both full-length and short version mRNA were found in all cells examined but in different ratios depending on cell type. Purified hippocampal and cortical neurons produce more short version than full-length MONaKA mRNA (FIG. 4A,B, compare lanes 1, 3 with 2, 4). Glial cells, conversely, have more full-length than short version mRNA (FIG. 4A,B, compare lanes 5, 7, 9 with 6, 8, 10). The findings that both the full-length and short forms of MONaKA are present in the nervous system, and that they exhibit differential expression ratios in neurons and glia, are intriguing, and suggest that the two forms of MONaKA may play different roles in different cell types.

Example 4

MONaKA Binds to Na,K-ATPase βSubunits

To explore the physiological role of MONaKA, both the short and full-length versions were used as bait in a yeast two-hybrid screen. These baits were screened against a mouse brain cDNA library and a mouse embryo cDNA library. Approximately 3 million mating yeast colonies were screened for MONaKA-interacting proteins. Among the positive clones, 12 exhibited sequence identity to the C-terminal domain of the β1 subunit of the Na,K-ATPase. One of the 12 clones encoded amino acid residues 110-277 of this 304 amino acid protein, and the remaining 11 encoded amino acids 110-273 (FIG. 5A). Another nine positive clones were found to encode amino acids 120-258 of the 278 amino acid β3 subunit of the Na,K-ATPase (FIG. 5A). Approximately half of these positive clones were isolated using full-length MONaKA and the other half using short MONaKA as bait. These results are consistent with the possibility that both the short and full-length versions of MONaKA interact with the plasma membrane Na,K-ATPase.

Figure 5:
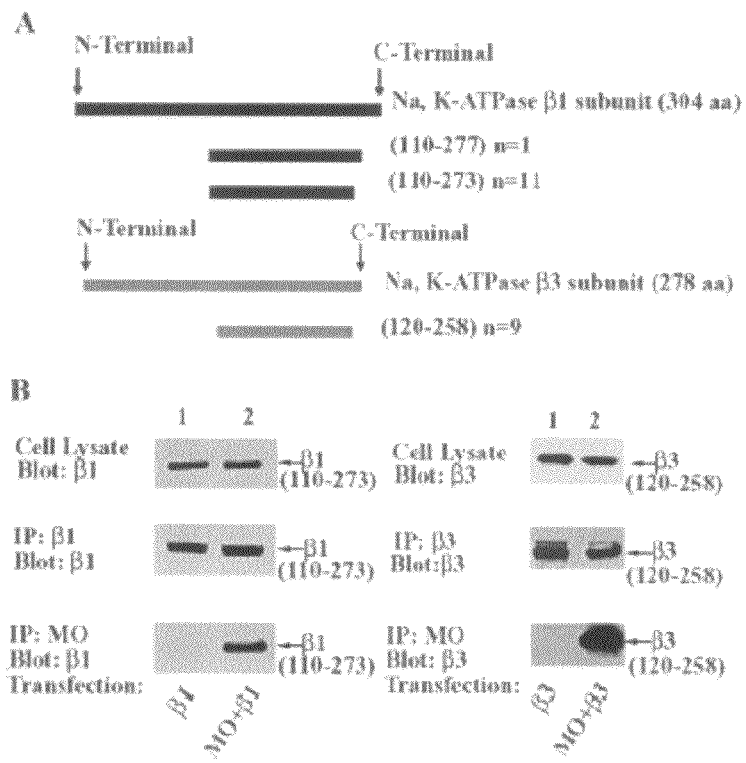
FIGS. 5A-B show that MONaKA binds to C-terminal fragments of Na,K-ATPase subunits.
Figure 6:
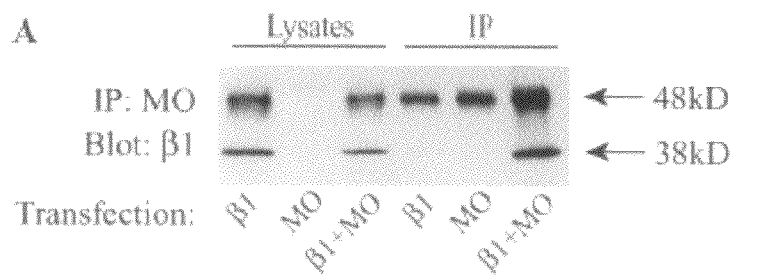
FIGS. 6A-B show Coimmunoprecipitation of MONaKA and β1 subunit. HA-tagged full-length MONaKA was cotransfected with Myc-tagged Na,K-ATPase β1 subunit. Western blot of cell lysates demonstrates that both the glycosylated (48 kDa) and nonglycosylated (38 kDa) forms of the β1 subunit (FIG. 6A, lysates) as well as MONaKA (FIG. 6B, lysates) are both expressed. The β1 subunit can be detected in aMONaKA immunoprecipitate (FIG. 6A), and, conversely, MONaKA can be detected in a β1 subunit immunoprecipitate (IP) (FIG. 6B), when the β1 subunit and MONaKA are transfected together. Vector transfection alone showed no bands in either direction (data not shown). Immunoprecipitation antibodies were either anti-Myc (β1) or anti-HA (MONaKA), with detection antibodies either anti-Myc or anti-MONaKA. The prominent 48 kDa band in the β1 and MOIP lanes in FIG. 6A is IgG. The 65 kDa band in the MO IP lane in FIG. 6B is probably MO coimmunoprecipitating with endogenous b-subunit.
Figure 6:
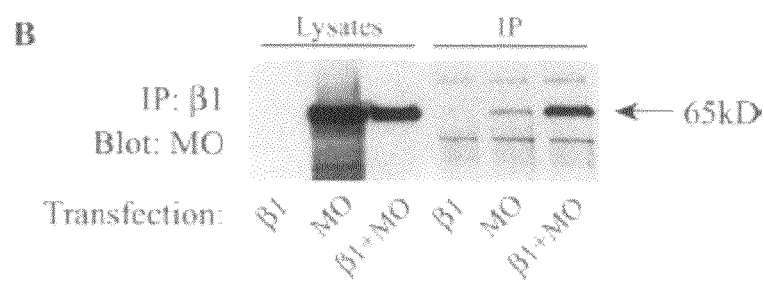

To confirm the results of the yeast two-hybrid screen, the C-terminal fragments of the Na,K-ATPase β1 and β3 subunits isolated from the screen were cloned into mammalian cell expression vectors with epitope tags. As shown in FIG. 5B, both the β1 subunit: fragment (left) and the β3 subunit fragment (right) coimmunoprecipitate with MONaKA. Communoprecipitation in the other direction gave similar results (data not shown). This finding confirms that these C-terminal fragments of the β1 and β3 subunits bind to MONaKA under coimmunoprecipitation conditions. Using a similar approach, we also tested the interaction of full-length Na,K-ATPase β1 subunit with MONaKA. As shown in FIG. 6, immunoprecipitation in both directions results in the coimmunoprecipitation of the β1 subunit and MONaKA. The results shown in FIGS. 5 and 6 were obtained using full-length MONaKA, but identical results were obtained with the short splice variant (data not shown). Together, these results demonstrate clearly that MONaKA is a binding partner for the Na,K-ATPase βsubunits in mammalian cells.

Example 5

Figure 7:
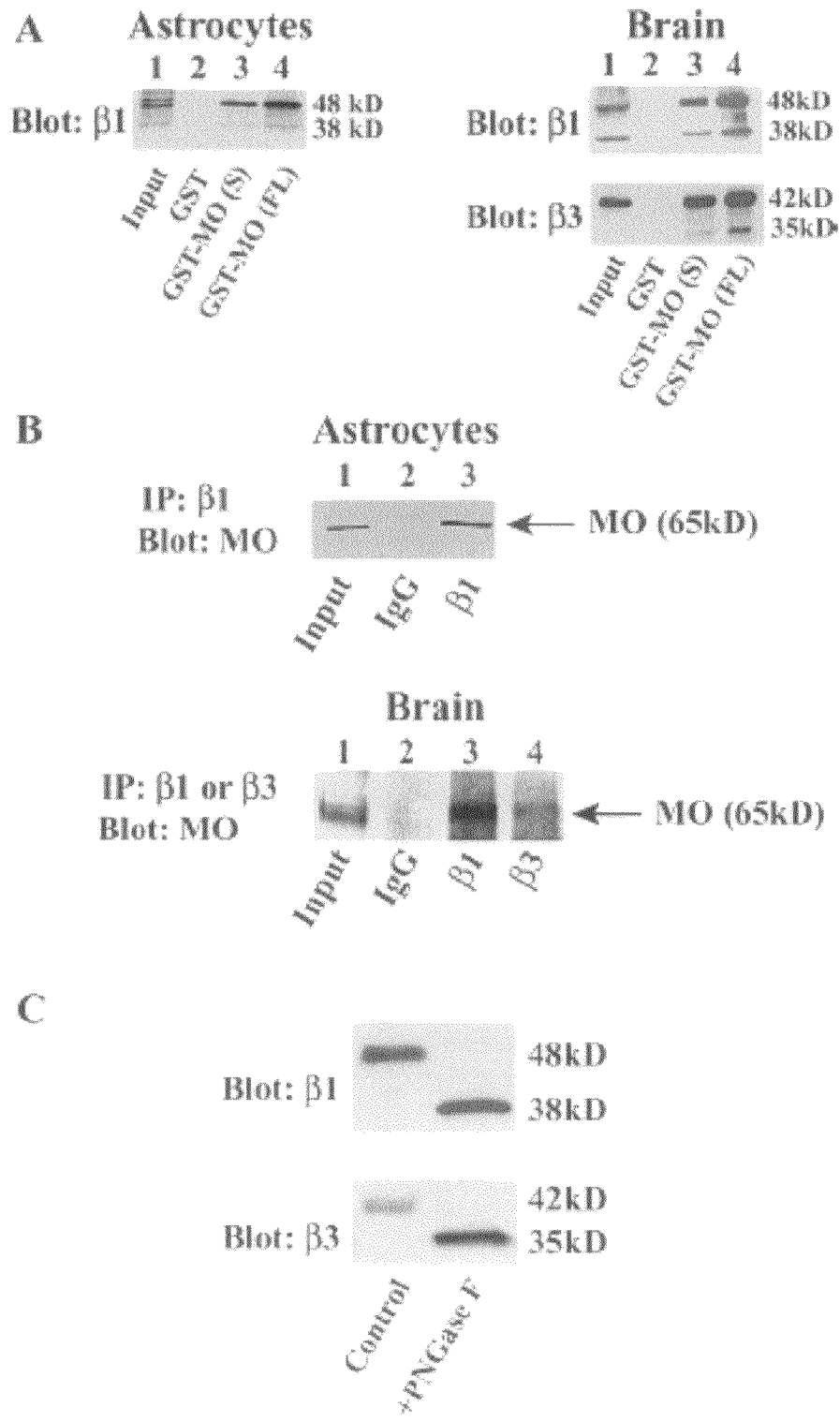
FIGS. 7A-C show that MONaKA interacts with native Na,K-ATPase β1 and β3 subunits.

MONaKA is Associated with Na,K-ATPase β1 and β3 Subunits in Native Cells and Tissue To determine whether MONaKA interacts with Na,K-ATPase βsubunits in native cells and tissue, GST-MONaKA fusion proteins were constructed using both the short and full-length splice variants. As shown in FIG. 7A, GST-MONaKA can pull down both the glycosylated and nonglycosylated forms of βsubunit protein from purified cultured mouse astrocytes (left) and from whole mouse brain (right). Both full-length and short GST-MONaKA are effective in pulling down the βsubunits (lanes 3 and 4), whereas GST alone is without effect (lane 2). Similarly, as shown in FIG. 7B, MONaKA coimmunoprecipitates with βsubunits from cultured astrocytes (top) and whole mouse brain (bottom). Thus, the interaction between MONaKA and Na,K-ATPase βsubunits occurs not only in transfected cells but also in native tissues.

Example 6

MONaKA is Distributed in Both Plasma Membrane and Cytoplasm in the Brain

Figure 8:
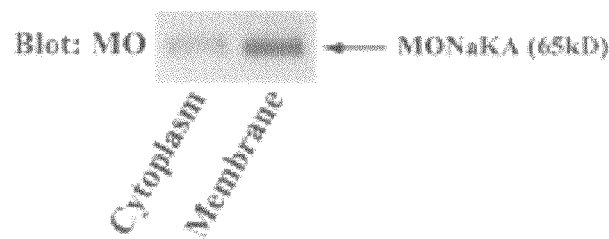
FIGS. 8A-B show that MONaKA is associated with the plasma membrane.
Figure 8:
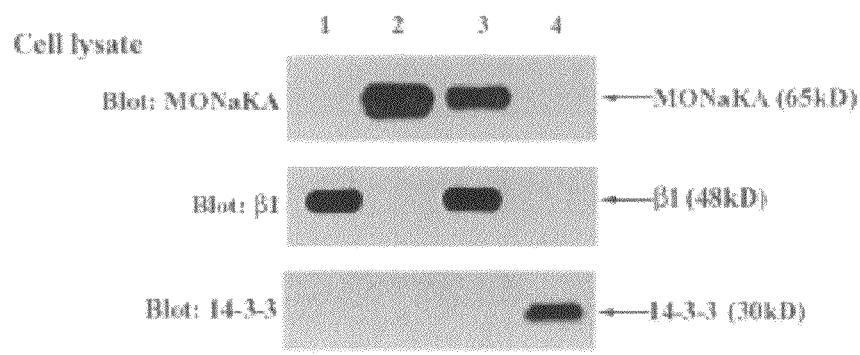
Figure 8:
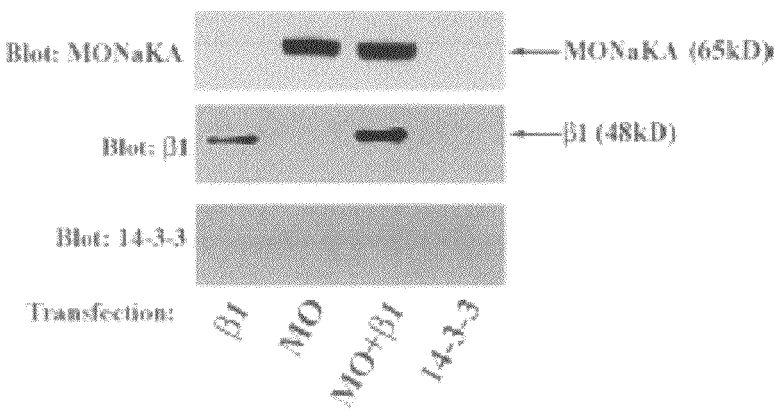

Although immunohistochemical analysis suggested that much of MONaKA in neurons and glia is localized in the cytoplasm (FIGS. 2, 3), the resolution of this method is not sufficient to determine whether any of the protein is associated with the plasma membrane in which the Na,K-ATPase resides. To examine this, two different methods were used: (1) Western blot analysis of separated brain membranes and cytoplasm, and (2) cell surface biotinylation. For Western blot analysis, mouse brain membranes were isolated and compared them with samples of brain cytoplasm. As shown in FIG. 8A, both the brain cytoplasm and brain membrane fractions contain MONaKA protein. Using gel densitometric quantitation, we found that approximately two-thirds of MONaKA protein is associated with the membrane, with the remaining one-third found in the cytoplasm.

As a secondary confirmation, a surface biotinylation reagent was used to label with biotin all proteins that have a portion of their sequence outside the plasma membrane. After the removal of the biotinylation reagent, biotinylated proteins were isolated by precipitation with avidin beads. As shown in FIG. 8B, MONaKA is present in the avidin precipitate from tsA201 cells, whether it was transfected alone (lane 2) or together with the β1 subunit of the Na,K-ATPase (lane 3). In contrast, when a similar experiment was performed in cells transfected with the ζ isoform of 14-3-3, which is known to be exclusively a cytoplasmic protein, no 14-3-3 is found in the avidin precipitate (lane 4). To test the possibility that MONaKA is not itself an intrinsic membrane protein but rather binds to some other membrane protein that can react with biotin, the avidin precipitate was washed with SDS at concentrations ranging from 2 to 10% before separation of the proteins on polyacrylamide gels. This treatment disrupts protein-protein interactions such that only the biotinylated proteins themselves would remain present in the avidin precipitate. MONaKA is still present in the avidin precipitate after this stringent treatment (data not shown), suggesting that at least some proportion of the protein behaves as an intrinsic membrane protein in these heterologous cells. In addition, the β1 subunit of Na,K-ATPase, which is known to be membrane bound, is also present after the SDS wash (data not shown), confirming that the avidin-biotin interaction survives this stringent treatment.

Example 7

MONaKA Modulates the Na,K-ATPase

Figure 9:
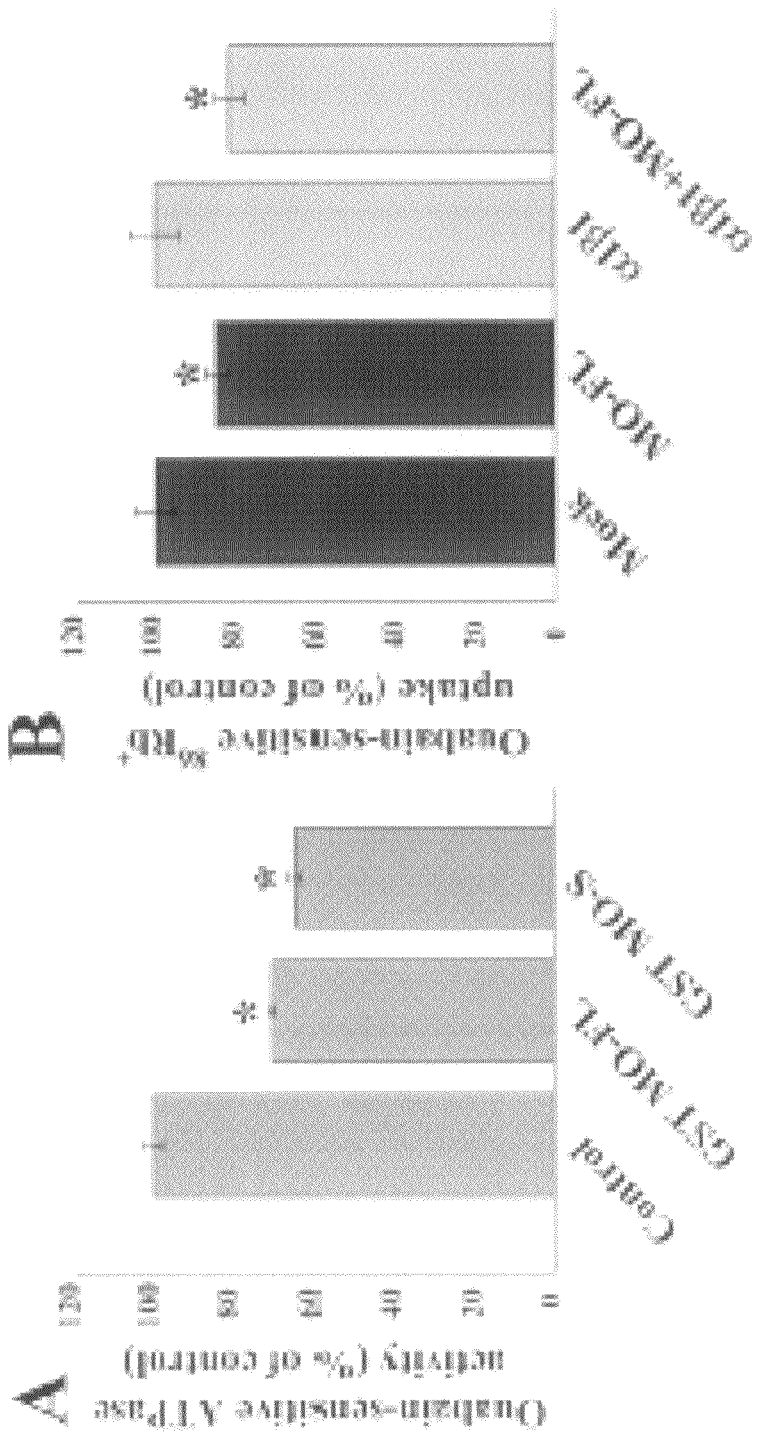
FIGS. 9A-B show that GST MONaKA inhibits Na,K-ATPase activity in vitro and $^{86}Rb^+$ uptake in intact cells.

To determine whether the binding of MONaKA to Na,K-ATPase β subunits can modulate the properties of the protein, it was tested whether MONaKA can influence the ATPase activity in vitro. A standard protocol was used for the partial purification of mouse brain Na,K-ATPase. The generation of inorganic phosphate from ATP by this membrane fraction was measured with a colorimetric assay, and the ouabain-sensitive fraction (~90%) of the total ATPase activity was taken as the activity attributable to the plasma membrane Na,K-ATPase. When purified GST-MONaKA fusion protein (either short or full-length) is added to this in vitro assay, the ATPase activity is inhibited by 30-38% (FIG. 9A). In contrast, neither GST-Drosophila Slob nor GST alone inhibits the ATPase activity (data not shown). These data are consistent with the possibility that MONaKA binding to Na,K-ATPase β subunit can acutely influence the enzymatic activity of the Na,K-ATPase. Similar results were also obtained when crude membranes were prepared from cultured astrocytes (data not shown).

To determine whether MONaKA can also influence the ion transport activity of the Na,K-ATPase, $^{86}Rb^+$ uptake into intact cells was examined via the Na,K-ATPase. tsA201 cells were transfected, and $^{86}Rb^+$ uptake was measured as described in Materials and Methods. As shown in FIG. 9B, endogenous ouabain-sensitive (~90% of the total) $^{86}Rb^+$ uptake is reduced 19% in MONaKA transfected cells (FIG. 9B, left two lanes). The tsA201 cells are derived from HEK296 cells, which contain endogenous Na,K-ATPase as well as MONaKA (confirmed by RT-PCR; data not shown). In addition, cotransfection of MONaKA together with Na,K-ATPase α1 and β1 subunits also decreases ouabain-sensitive $^{86}Rb^+$ uptake to approximately the same extent when compared with α1β1 transfected controls (FIG. 9B, right two lanes). MONaKA cotransfection does not alter the expression level of the Na,K-ATPase α1 and β1 subunits (data not shown).

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. An isolated nucleic acid molecule consisting of SEQ ID NO: 8.

2. The isolated nucleic acid molecule of claim 1, wherein the nucleic acid molecule is cDNA.

3. A vector comprising the isolated nucleic acid molecule of claim 1.

4. The vector of claim 3, further comprising a promoter of RNA transcription, or an expression element operatively linked to the nucleic acid.

5. The vector of claim 4, wherein the promoter comprises a bacterial, yeast, insect or mammalian promoter.

6. The vector of claim 5, wherein the vector is a plasmid, cosmid, yeast artificial chromosome (YAC), bacterial artificial chromosome (BAC), adenovirus, adeno-associated virus, retrovirus, P1 Phage (P1), bacteriophage or eukaryotic viral DNA.

* * * * *